United States Patent [19]
Paoletti et al.

[11] Patent Number: 5,641,490
[45] Date of Patent: Jun. 24, 1997

[54] INFECTIOUS BURSAL DISEASE VIRUS RECOMBINANT POXVIRUS VACCINE

[75] Inventors: Enzo Paoletti, Delmar; Jill Taylor, Albany; Russell Gettig, Averill Park, all of N.Y.

[73] Assignee: Virogenetics Corporation, Troy, N.Y.

[21] Appl. No.: 303,124

[22] Filed: Sep. 7, 1994

Related U.S. Application Data

[63] Continuation of Ser. No. 918,311, Jul. 21, 1992, abandoned, which is a continuation-in-part of Ser. No. 736,254, Jul. 26, 1991, abandoned, and Ser. No. 847,951, Mar. 6, 1992, abandoned, which is a continuation-in-part of Ser. No. 713,967, Jun. 11, 1991, abandoned, which is a continuation-in-part of Ser. No. 666,056, Mar. 7, 1991, Pat. No. 5,364,773.

[51] Int. Cl.$^6$ .................. A61K 39/275; A61K 39/295; A61K 39/12; C12N 7/01

[52] U.S. Cl. .................. 424/199.1; 435/235.1; 435/320.1; 435/69.1; 435/69.3; 424/204.1; 424/232.1; 935/65

[58] Field of Search .................. 435/235.1, 69.1, 435/69.3, 91, 172.3, 240.1, 320.1; 424/199.1, 204.1, 232.1; 935/9, 32, 34, 57, 65, 70; 536/23.1, 23.72

[56] References Cited

U.S. PATENT DOCUMENTS

| | | | |
|---|---|---|---|
| 5,093,258 | 3/1992 | Cohen et al. | 435/235.1 |
| 5,151,267 | 9/1992 | Babiuk | 424/186.1 |
| 5,180,675 | 1/1993 | Drillien et al. | 435/235.1 |

OTHER PUBLICATIONS

Müller et al., J. Gen. Virology 38, 135–147 (1977).
Azad et al Vaccines 90 pp. 59–62 (1990) Cold Spring Harbor Laboratory Press, CSH, NY.
Lukert, P.D. and L.A. Mazariegos, J. Am. Vet. Med. Assoc. 187, 306 (Abstr) (1985).
Jagadish et al Virology vol. 184 pp. 805–807 (1991).
Taylor et al J. Virol vol. 64 pp. 1441–1450 (1990).
Allan, W.H., J.T. Faragher, and G.A. Cullen, Vet. Rec. 90, 511–512 (1972).
Azad, A.A., S.A. Barrett, and K.J. Fahey, Virology 143, 35–44 (1985).
Azad, A.A., K.J. Fahey, S. Barrett, K. Erny and P. Hudson, Virology 149, 190–198 (1986).
Azad, A.A., M.N. Jagadish, M.A. Brown, and P.J. Hudson, Virology 161, 145–152 (1987).
Baxendale, W. and Lutticken, Dev. Biol. Stand. 51, 211–219 (1981).
Becht, H., H. Muller, and H.K. Muller, J. Gen. Virol. 69, 631–640 (1988).
Brown, F., Intervirology 25, 141–143 (1986).
Burkhardt, E. and H. Muller, Archives of Virology 94, 297–303 (1987).
Clewell, D.B., J. Bacteriol. 110, 667–676 (1972).
Clewell, D.B. and D.R. Helinski, Proc. Natl. Acad. Sci. USA 62, 1159–1166 (1969).
Dobos,P., J. Virol. 32, 1046–1050 (1979).
Dobos, P., B.J. Hill, R. Hallett, D.T. Kells, H. Becht, and D. Teninges, J. Virol. 32, 593–605 (1979).
Duncan, R., E. Nagy, P.J. Krell and P. Dobos, J. Virol. 61, 3655–3664 (1987).
Edbauer, C., R. Weinberg, J. Taylor, A. Rey–Senelonge, J.F. Bouquet, P. Desmettre and E. Paoletti, Virology 179, 901–904 (1990).
Fahey, K.J., I.J. O'Donnell, and A.A. Azad, J. Gen. Virol. 66, 1479–1488 (1985a).
Fahey, K.J., I.J. O'Donnell, and T.J. Bagust, J. Gen. Virol. 66, 2693–2702 (1985b).
Fahey K.J., K. Erny and J. Crooks, J. Gen. Virol. 70, 1473–1481 (1989).
Guo, P., S. Goebel, S. David, M.E. Perkus, B. Langest, P. Desmettre, G. Allen, and E. Paoletti, J. Virol. 63, 4189–4198 (1989).
Hudson, P.J., N.M. McKern, B.E. Power, and A.A. Azad, Nucl. Acids. Res. 14, 5001–5012 (1986).
Jackwood, D.J., Y.M. Saif, and J.H. Hughes, Avian Dis. 28, 990–1006 (1984).
Jagadish, M.N., V.J. Staton, P.J. Hudson, and A.A. Azad, J. Virol. 62, 1084–1087 (1988).
Kaufer, I. and E. Weiss, Infect. Immun. 27, 364–367 (1980).
Kibenge, F.S.B., A.S. Dhillon, and R.G. Russell, J. Gen. Virol. 69, 1757–1775 (1988).
Ley, D.H., R. Yamamoto, and A.A. Bickford, Avian Diseases 23, 219–224 (1979).
Lucio, B. and S.B. Hitchner, Avian Dis. 23, 466–478 (1979).
Lukert, P.D. and S.B. Hitchner, In Diseases of Poultry 8th edition, eds. M.S. Hofstad, H.J. Barnes, B.W. Calnek, W.M. Reid and H.W. Yoder (Iowa State University Press–Ames) pp. 566–576 (1984).
Lukert, P.D. and Y.M. Saif, In Diseases of Poultry 9th edition, eds. B.W. Calnek, H.J. Barnes, C.W. Beard, W.M. Reid and H.W. Yoder (Iowa State University Press–Ames) pp. 648–663 (1991).
Macreadie, I.G., P.R. Vaughan, A.J. Chapman, N.M. McKern, M.N. Jagadish, H.G. Heine, C.W. Ward, K.J. Fahey, and A.A. Azad, Vaccine 8, 549–552 (1990).
Matthews, R.E.F., Intervirology 17, 42–44 (1982).
McFarran, J.B., M.S. McNulty, E.R. McKillop, T.J. Connor, R.M. McCracken, D.S. Collins, and G.M. Allen, Avian Pathol. 9, 395–404 (1980).
McNulty, M.S. and Y.M. Saif, Avian Dis. 32, 374–375 (1988).
Muller, H., Arch. Virol. 87, 191–203 (1986).
Muller, H. and H. Betch, J. Virol. 44, 384–392 (1982).
Nagy, E., R. Duncan, P. Krell, and P. Dobos, Virology 158, 211–217 (1987).

(List continued on next page.)

*Primary Examiner*—Mary E. Mosher
*Attorney, Agent, or Firm*—Curtis, Morris & Safford, P.C.

[57] ABSTRACT

What is described is a recombinant poxvirus, such as fowlpox virus, containing foreign DNA from infectious bursal disease virus. What is also described is a vaccine containing the recombinant poxvirus for inducing an immunological response in a host animal inoculated with the vaccine.

7 Claims, 4 Drawing Sheets

OTHER PUBLICATIONS

Panicali, D. and E. Paoletti, Proc. Natl. Acad. Sci. USA 79, 4927–4931 (1982).

Perkus, M.E., K. Limbach, and E. Paoletti, J. Virol. 63, 3829–3836 (1989).

Piccini, A., M.E. Perkus, and E. Paoletti, In Methods in Enzymology, vol. 153, eds. Wu, R., and Grossman, L., (Academic Press) pp. 545–563 (1987).

Sambrook, J., E.F. Fritsch, and T. Maniatis, In Molecular cloning: A laboratory manual, 2nd edition (Cold Spring Harbor Press, NY) (1989).

Schat, K.A., B. Lucio, and J.C. Carlisle, Avian Dis. 25, 996–1004 (1981).

Skeeles, J.K., P.D. Lukert, E.V. De Buysscher, O.J. Fletcher, and J. Brown, Avian Dis. 23, 95–106 (1979).

Snyder, D.B., D.P Lana, B.R. Cho, and W.W. Marquardt, Avian Dis. 32, 527–534 (1988).

Spies, U., H. Muller, and H. Becht, Virus Res. 8, 127–140 (1987).

Taylor, J., C. Edbauer, A. Rey–Senelonge, J.F. Bouquet, E. Norton, S. Goebel, P. Desmettre and E. Paoletti, J. Virol. 64, 1441–1450 (1990).

Taylor, J., R. Weinberg, Y. Kawaoka, R. Webster and E. Paoletti, Vaccine 6, 504–508 (1988).

Winterfield, R.W., A.S. Dhillon, H.L. Thacker, L.J. Alby, Avian Dis. 24, 179–188 (1980).

Bayliss, C.D., U. Spies, K. Shaw, R.W. Peters, A. Papageorgiou, H. Muller, and M.E.G. Boursnell, J. Gen. Virol. 71, 1303–1312 (1990).

Bertholet, C., R. Drillien, and R. Wittek, Proc. Natl. Acad. Sci. U.S.A. 82, 2096–2100 (1985).

Casadaban, M.J., A. Martinez–Arias, S.K. Shapiro and J. Chou, Methods in Enzymol. 100, 293–307 (1983).

Fahey, J.J., I.J. O'Donnell, and T.J. Bagust, J. Gen. Virol. 66, 2693–2702 (1985b).

Kibenge, F.S.B., D.J. Jackwood, and C.C. Mercado, J. Gen. Virol. 71, 569–577 (1990).

Langford, C.J., S.J. Edwards, G.L. Smith, G.F. Mitchell, B. Moss, D.J. Kemp, and R.F. Anders, Mol. Cell. Biol. 6, 3191–3199 (1986).

Paoletti, E., B.R. Lipinskaks, C. Samsonoff, S. Mercer, and D. Panicali, Proc. Natl. Acad. Sci. U.S.A. 81, 193–197 (1984).

Shapira, S.K., J. Chou, F.V. Richaud, and M.J. Casadaban, Gene 25, 71–82 (1983).

Tartaglia, J., J. Winslow, S. Goebel, G.P. Johnson, J. Taylor, and E. Paoletti, J. Gen. Virol. 71, 1517–1524 (1990).

Vijaya, S., N. Elango, F. Zavala, and B. Moss, Mol. Cell. Biol. 8, 1709–1714 (1988).

Winterfield, R.W., A.M. Fadly, and A. Bickford. Avian Dis. 16, 622–632 (1972).

```
        10         20         30         40         50         60         70         80         90        100
GATATCTGTGGTCTATATACTACACCCTACCGATATTAACCAACGAGTTTCTCACAGAAAAACTTGTTTAGTAGATAGAGATTCTTTGATTGTGTTTA 110        120        130        140        150        160        170        180        190        200
AAAGAAGTACCAGTGTAAAAAGTGTGGCATATGCATAGAGAAATAAACAAAAAACATATTTCCGAACAGTATTTTGGAATTCTCCCAAGTTGTAAACATAT 210        220        230        240        250        260        270        280        290        300
TTTTTGCCTATCATGTATAAGACGTTGGGCAGATACTACCAGAGAAATACAGATACTGTCCTGAATGTAGAATAGTTTTTCCTTTTCATAATA 310        320        330        340        350        360        370        380        390        400
CCCAGTAGGTATTGGATAGATAATAAATATGATAAAAAAATATTATATAATAGATATATAGAGAAAATGATTTTACAAAAATAACCTATAAGAACAATAAAA 410        420        430        440        450        460        470        480        490        500
ATATAATTACATTTACGGAAAAATAGCTGGTTTTAGTTTACCAACTTAGAGTAATTATCATATTGAATCTATATTGTTTTTAGTTATATAAAAACATGAT 510        520        530        540        550        560        570        580        590        600
TAGCCCCCAATCGGATGAAATATAAAAGATGTTGAGAATTTCGAATACAACAAAAGAGGAATCGTACGTTGTCCATATCCAAACATATAAATAAAAAT 610        620        630        640        650        660        670        680        690        700
TCAAAAGTAGTATTATACTGGATGTTTAGAGATCAACGTGTACAAGATAATTGGGCTTTAATTTACGCACAACGATTAGCGTTAAAACTCAAAATACCTC 710        720        730        740        750        760        770        780        790        800
TAAGAATATGCTTTTGTGTCGTGCCAAAATTTCACACTACTTCTAGACACTTTATGTTTTTTAATATCCGGTTCTTAAAGAAGTCGCGGAAGAATGTA 810        820        830        840        850        860        870        880        890        900
AAAGACTATGTATAGGGTTTTCATTGATATATGGGCGTACCAAAAGTAATAATTCCGTAGTAAAAAAATACAGAGTGGGAGTAATCATAACGGATTT 910        920        930        940        950        960        970        980        990       1000
CTTTCCATTACGTGTTCCCGAAAGATTAATGAAACAGACTGTAATATCTCTTCCAGATAATAACATACCTTTATACAAGTAGACGCTCATAATATAGTACCT 1010       1020       1030       1040       1050       1060       1070       1080       1090       1100
TGTTGGGAAGCTTCTGATAAGAAGAATACGGTGCACGAACTTTAAGAAAAAGATATTTGATAATTATGAATAAATTATGACAGAATTCCTGTTGTTC 1110       1120       1130       1140       1150       1160       1170       1180       1190       1200
GTAAACATCCATACGGTCCATTTTCTATATCTATTGCAAAACCCAAAATATATATCATTAGACAAGACGGTATTACCGTAAAATGGGCAACGCCTGGAAC 1210       1220       1230       1240       1250       1260       1270       1280       1290       1300
AAAAGCTGGAATAATTGTTTAAAAGAATTTATAAAAAACAGATTACCGTCATACGACGCGGATCATAACAATCCTACGTGTGACGCTTTGAGTAACTTA
```

FIG. 1A

```
     1310      1320      1330      1340      1350      1360      1370      1380      1390      1400
TCTCCGTGGCTACATTTTGGTCATGTATCCGCACAACGTGTTGCCTTAGAAGTATTAAAATGTATACGAGAAAGCAAAAAACGTTGAAACGTTTATAG
     1410      1420      1430      1440      1450      1460      1470      1480      1490      1500
ATGAAATAATTGTAAGAAGAGAACTATCGGATAATTTTTGTTACTATATGATAGTATCCAGTCTCATTCATGGGTTAGAAAAACATT
     1510      1520      1530      1540      1550      1560      1570      1580      1590      1600
AGAAGATCACATTAATGATCCTAGAAAGTATATATATTCCATTAAACAACTCGAAAAAGCGGAAACTCATGATCCTCTATGGAACGCGTCACAAATGCAG
     1610      1620      1630      1640      1650      1660      1670      1680      1690      1700
ATGGTGAGAGAAGGAAAAATGCATAGTTTTTTACGAATGTATTGGGCTAAGAAGATACTTGAATGGACTAGAACACCTGAAGACGCTTTGAGTTATAGTA
     1710      1720      1730      1740      1750      1760      1770      1780      1790      1800
TCTATTTGAACAACAGTACGAACTAGAGGCACGGATCCTAACGGATACGTAGGTTGTATGTGGTCTATTTGCGGATTACACGATAGAGCGTGGAAAGC
     1810      1820      1830      1840      1850      1860      1870      1880      1890      1900
AAGACCGATATTTGGAAAGATAAGATAATTATGAGAGTTCTAAGAAGAAATTTGATGTTGCTGTATTTATACAGAAATACAATTAAGATAAAATAA
     1910      1920      1930      1940      1950      1960      1970      1980      1990      2000
TATACAGCATTGTAACCATCGTCATCCGTTATACGGGGAATAATATTACCATACAGTATTATTAAATTTTCTTACGAGAATATAGATCGGTATTTATCG
     2010      2020      2030      2040      2050      2060      2070      2080      2090      2100
TTAGTTTATTTTACATTTATTAATTAAACATGTCTACTATTACCTGTTATGGAAATGACAAATTTAGTTATATAATTATGATAAATTAAGATAATAAT
     2110      2120      2130      2140      2150      2160      2170      2180      2190      2200
AATGAAATCAAATAATTATGTAAATGCTACTAGATTATGTGAATTACGAGGAAGAAAGTTTACGAACTGGAAAAAATTAAGTGAATCTAAAATATTAGTC
     2210      2220      2230      2240      2250      2260      2270      2280      2290      2300
GATAATGTAAAAAAAAATCAAATAATAAATGATAAAACCAGTAAGTTAAAAACGGATATGATTATACGTTAAGGATATCATAAAGGAAGAGATACTTGCGGTT
     2310      2320      2330      2340      2350      2360      2370      2380      2390      2400
ACTATGTACACCAAGATCTGGTATCTTCTATCAAATTGGATATCTCCGTTATTCGCCGTTAAGGTAAATAAAATTATTAACTATTATATGTAATGA
     2410      2420      2430      2440      2450      2460      2470      2480      2490      2500
ATATGATATACGACTTAGCGAAATGGAATCTGATATGACAGAAGTAGTTGATAAATTAGTAGGAGGATACAATGATGAAATAGCAGAAATA
```

```
     2510      2520      2530      2540      2550      2560      2570      2580      2590      2600
ATATATTTGTTTAATAAATTTATAGAAAAATATATTGCTAACATATCGTTATCAACTGAATTATCTAGTATATTAAATAATTTATAAATTTATAAATT 2610      2620      2630      2640      2650      2660      2670      2680      2690      2700
TTAATAAAAAATACAATAACGACATAAAGATATTTAATCTTTAATTCTTGATCTGAAAAACACATCTATAAAACTAGATAAAAAGTTATTCGATAAAGAT 2710      2720      2730      2740      2750      2760      2770      2780      2790      2800
AATGAATCGAACGATGAAAAATTGGAAACAGAAGTTGATAAGCTAATTTTTTCATCTAAATAGTATTATTTATTGAAGTACGAAGTTTACGTTA 2810      2820      2830      2840      2850      2860      2870      2880      2890      2900
GATAAATAATAAGGTCGATTTTTACTTTGTTAAAATATCAAATATGTCATTATCTGATAAAGATACAAAAACACACGGTGATTATCAACCATCTAACGAA 2910      2920      2930      2940      2950      2960      2970      2980      2990      3000
CAGATATTACAAAAAATACGTCGGACTATGGAAAACGAAGCTGATAGCCTCAATAGAGAAGAAGCATTAAAGAAATTGTTGTAGATGTTATGAAGAATTGGG 3010      3020      3030      3040      3050      3060      3070      3080      3090      3100
ATCATCCTCAACGAAGAAATAGATAAAGTTCTAAACTGGAAAAATGATACATTAAACGATTTAGATCATCTAAATACAGATGATAATATTAAGGAAATCA 3110      3120      3130      3140      3150      3160      3170      3180      3190      3200
TACAATGTCTGATTAGAGAATTTGCGTTTAAAAAGATCAATTCTATTATGTATAGTTATGCTATGGTAAAACTCAATTCAGATAACGAACATTGAAAGAT 3210      3220      3230      3240      3250      3260      3270      3280      3290      3300
AAAATTAAGGATTATTTTATAGAAACTATTCTTAAAGAACAAACGTGGTTATAAACAAAGCCATTACCCGGATTGGAAACTAAAATACTAGATAGTATTA 3310      3320      3330      3340      3350      3360      3370      3380      3390      3400
TAAGATTTTAAAAACATAAATAAATAATAGGTTTTTATAGATTGACTTATTATTATACAATATGGATAAAGATATATCAACTAGAAAGTTGAATGACGGA 3410      3420      3430      3440      3450      3460      3470      3480      3490      3500
TTCTTAATTTTATATTTGATTCAATAGATTCATGTCGTGTAATCATTTATAAATATATCAGCGTTACTAGCTAAGAAAAACAAGGACTTTA 3510      3520      3530      3540      3550      3560      3570      3580      3590      3600
ATGAATGGCTAAAGATAGAATCATTTAGAGAAATAATTTAGATAAAATTAATTACGATCTAGGACAACGATATTGTGAAGAACTTACGGCGCA 3610      3620      3630      3640      3650      3660
TCACATTCCAGTGTAATTATTGAGGTCAAAGCTAGTAACTTAATAGATGACAGGAAGCTG
```

```
   1 GATATCTGTG GTCTATATAT ACTACACCCT ACCGATATTA ACCAACGAGT TTCTCACAAG
  61 AAAACTTGTT TAGTAGATAG AGATTCTTTG ATTGTGTTTA AAAGAAGTAC CAGTAAAAAG
 121 TGTGGCATAT GCATAGAAGA AATAAACAAA AAACATATTT CCGAACAGTA TTTTGGAATT
 181 CTCCCAAGTT GTAAACATAT TTTTTGCCTA TCATGTATAA GACGTTGGGC AGATACTACC
 241 AGAAATACAG ATACTGAAAA TACGTGTCCT GAATGTAGAA TAGTTTTTCC TTTCATAATA
 301 CCCAGTAGGT ATTGGATAGA TAATAAATAT GATAAAAAAA TATTATATAA TAGATATAAG
 361 AAAATGATTT TTACAAAAAT ACCTATAAGA ACAATAAAAA TATAATTACA TTTACGGAAA
 421 ATAGCTGGTT TTAGTTTACC AACTTAGAGT AATTATCATA TTGAATCTAT ATTGTTTTTT
 481 AGTTATATAA AAACATGATT AGCCCCCAAT CGGATGAAAA TATAAAGAT GTTGAGAATT
 541 TCGAATACAA CAAAAGAGG AATCGTACGT TGTCCATATC CAAACATATA AATAAAAATT
 601 CAAAAGTAGT ATTATACTGG ATGTTTAGAG ATCAACGTGT ACAAGATAAT TGGGCTTTAA
 661 TTTACGCACA ACGATTAGCG TTAAAACTCA AAATACCTCT AAGAATATGC TTTTGTGTCG
 721 TGCCAAAATT TCACACTACT ACTTCTAGAC ACTTTATGTT TTTAATATCC GGTCTTAAAG
 781 AAGTCGCGGA AGAATGTAAA AGACTATGTA TAGGGTTTTC ATTGATATAT GGCGTACCAA
 841 AAGTAATAAT TCCGTGTATA GTAAAAAAAT ACAGAGTCGG AGTAATCATA ACGGATTTCT
 901 TTCCATTACG TGTTCCCGAA AGATTAATGA AACAGACTGT AATATCTCTT CCAGATAACA
 961 TACCTTTTAT ACAAGTAGAC GCTCATAATA TAGTACCTTG TTGGGAAGCT TCTGATAAAG
1021 AAGAATACGG TGCACGAACT TTAAGAAAAA AGATATTTGA TAAATTATAT GAATATATGA
1081 CAGAATTTCC TGTTGTTCGT AAACATCCAT ACGGTCCATT TTCTATATCT ATTGCAAAAC
1141 CCAAAAATAT ATCATTAGAC AAGACGGTAT TACCCGTAAA ATGGGCAACG CCTGGAACAA
1201 AAGCTGGAAT AATTGTTTTA AAAGAATTTA TAAAAAACAG ATTACCGTCA TACGACGCGG
1261 ATCATAACAA TCCTACGTGT GACGCTTTGA GTAACTTATC TCCGTGGCTA CATTTTGGTC
1321 ATGTATCCGC ACAACGTGTT GCCTTAGAAG TATTAAAATG TATACGAGAA AGCAAAAAAA
1381 ACGTTGAAAC GTTTATAGAT GAAATAATTG TAAGAAGAGA ACTATCGGAT AATTTTTGTT
1441 ACTATAACAA ACATTATGAT AGTATCCAGT CTACTCATTC ATGGGTTAGA AAAACATTAG
1501 AAGATACACAT TAATGATCCT AGAAAGTATA TATATTCCAT TAAACAACTC GAAAAAGCGG
1561 AAACTCATGA TCCTCTATGG AACGCGTCAC AAATGCAGAT GGTGAGAGAA GGAAAAATGC
1621 ATAGTTTTTT ACGAATGTAT TGGGCTAAGA AGATACTTGA ATGGACTAGA ACACCTGAAG
1681 ACGCTTTGAG TTATAGTATC TATTTGAACA ACAAGTACGA ACTAGACGGC ACGGATCCTA
1741 ACGGATACGT AGGTTGTATG TGGTCTATTT GCGGATTACA CGATAGAGCG TGGAAAGCAA
1801 GACCGATATT TGGAAAGATA AGATATATGA ATTATGAGAG TTCTAAGAAG AAATTTGATG
1861 TTGCTGTATT TATACAGAAA TACAATTAAG ATAAATAATA TACAGCATTG TAACCATCGT
1921 CATCCGTTAT ACGGGGAATA ATATTACCAT ACAGTATTAT TAAATTTTCT TACGAAGAAT
1981 ATAGATCGGT ATTTATCGTT AGTTTATTTT ACATTTATTA ATTAAACATG TCTACTATTA
2041 CCTGTTATGG AAATGACAAA TTTAGTTATA TAATTTATGA TAAAATTAAG ATAATAATAA
2101 TGAAATCAAA TAATTATGTA AATGCTACTA GATTATGTGA ATTACGAGGA AGAAAGTTTA
2161 CGAACTGGAA AAAATTAAGT GAATCTAAAA TATTAGTCGA TAATGTAAAA AAAATAAATG
2221 ATAAAACTAA CCAGTTAAAA ACGGATATGA TTATATACGT TAAGGATATT GATCATAAAG
2281 GAAGAGATAC TTGCGGTTAC TATGTACACC AAGATCTGGT ATCTTCTATA TCAAATTGGA
2341 TATCTCCGTT ATTCGCCGTT AAGGTAAATA AAATTATTAA CTATTATATA TGTAATGAAT
2401 ATGATATACG ACTTAGCGAA ATGGAATCTG ATATGACAGA AGTAATAGAT GTAGTTGATA
2461 AATTAGTAGG AGGATACAAT GATGAAATAG CAGAAATAAT ATATTTGTTT AATAAATTTA
2521 TAGAAAAATA TATTGCTAAC ATATCGTTAT CAACTGAATT ATCTAGTATA TTAAATAATT
2581 TTATAAATTT TATAAATTTT AATAAAAAAT ACAATAACGA CATAAAGATA TTTAATCTTT
2641 AATTCTTGAT CTGAAAAACA CATCTATAAA ACTAGATAAA AAGTTATTCG ATAAAGATAA
2701 TAATGAATCG AACGATGAAA AATTGGAAAC AGAAGTTGAT AAGCTAATTT TTTTCATCTA
2761 AATAGTATTA TTTTATTGAA GTACGAAGTT TTACGTTAGA TAAATAATAA AGGTCGATTT
2821 TTACTTTGTT AAATATCAAA TATGTCATTA TCTGATAAAG ATACAAAAAC ACACGGTGAT
2881 TATCAACCAT CTAACGAACA GATATTACAA AAAATACGTC GGACTATGGA AAACGAAGCT
2941 GATAGCCTCA ATAGAAGAAG CATTAAAGAA ATTGTTGTAG ATGTTATGAA GAATTGGGAT
3001 CATCCTCAAC GAAGAAATAG ATAAAGTTCT AAACTGGAAA AATGATACAT TAAACGATTT
3061 AGATCATCTA AATACAGATG ATAATATTAA GGAAATCATA CAATGTCTGA TTAGAGAATT
3121 TGCGTTTAAA AAGATCAATT CTATTATGTA TAGTTATGCT ATGGTAAAAC TCAATTCAGA
3181 TAACGAACAT TGAAAGATAA AATTAAGGAT TATTTTATAG AAACTATTCT TAAAGACAAA
3241 CGTGGTTATA AACAAAAGCC ATTACCCGGA TTGGAAACTA AAATACTAGA TAGTATTATA
3301 AGATTTTAAA AACATAAAAT TAATAGGTTT TTATAGATTG ACTTATTATA TACAATATGG
3361 ATAAAAGATA TATATCAACT AGAAAGTTGA ATGACGGATT CTTAATTTTA TATTATGATT
3421 CAATAGAAAT TATTGTCATG TCGTGTAATC ATTTTATAAA TATATCAGCG TTACTAGCTA
3481 AGAAAAACAA GGACTTTAAT GAATGGCTAA AGATAGAATC ATTTAGAGAA ATAATAGATA
3541 CTTTAGATAA AATTAATTAC GATCTAGGAC AACGATATTG TGAAGAACTT ACGGCGCATC
3601 ACATTCCAGT GTAATTATTG AGGTCAAAGC TAGTAACTTA ATAGATGACA GGACAGCTG
```

FIG. 2

INFECTIOUS BURSAL DISEASE VIRUS RECOMBINANT POXVIRUS VACCINE

CROSS REFERENCE TO RELATED APPLICATIONS

This application is a continuation of application Ser. No. 07/918,311, filed Jul. 21, 1992, now abandoned which is a continuation-in-part of application Ser. No. 07/736,254 filed Jul. 26, 1991, incorporated herein by reference, now abandoned, and also a continuation-in-part of application Ser. No. 07/847,951, filed Mar. 6, 1992, incorporated herein by reference, now abandoned, which is a continuation-in-part of 07/713,967 filed Jun. 11, 1991, now abandoned, which is a continuation-in-part of 07/666,056 filed Mar. 7, 1991, now U.S. Pat. No. 5,364,773.

FIELD OF THE INVENTION

The present invention relates to a modified poxvirus and to methods of making and using the same. More in particular, the invention relates to recombinant poxvirus, which virus expresses gene products of an infectious bursal disease virus (IBDV) gene, and to vaccines which provide protective immunity against IBDV infections.

Several publications are referenced in this application. Full citation to these documents is found at the end of the specification preceding the claims. These documents pertain to the field of this invention; and, each of the documents referenced in this application are hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. Nos. 5,110,587, 4,769,330, 4,722,848, and 4,603,112; the disclosures of each of these patents is incorporated herein by reference. Reference is also made to copending application Ser. No. 07/537,890, filed Jun. 14, 1990, also incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Sambrook et al., 1989).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

The technology of generating vaccinia virus recombinants has recently been extended to other members of the poxvirus family which have a more restricted host range. The avipox virus, fowlpox, has been engineered as a recombinant virus. This recombinant virus is described in PCT Publication No. WO89/03429, also incorporated herein by reference.

Fowlpox virus (FPV) has advantageously been engineered as a vector expressing antigens from poultry pathogens. The hemagglutinin protein of a virulent avian influenza virus was expressed in an FPV recombinant (Taylor et al., 1988). After inoculation of the recombinant into chickens and turkeys, an immune response was induced which was protective against either a homologous or heterologous virulent influenza virus challenge (Taylor et al., 1988). In addition, the surface glycoproteins (fusion and hemagglutinin) of a virulent strain of Newcastle Disease Virus have been expressed in an FPV vector and shown to induce a protective immune response (Taylor et al., 1990; Edbauer et al., 1990).

FPV is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of the virus causing a productive infection in any non-avian species including man. This host restriction provides an inherent safety barrier to transmission of the virus to other species and makes use of FPV as a vaccine vector in poultry an attractive proposition.

Infectious bursal disease, also known as Gumboro's disease, manifests itself in two ways. In chickens older than three weeks, infectious bursal disease virus (IBDV) can cause impaired growth and mortality losses of up to 20% (Lukert and Hitchner, 1984). In younger birds, the disease is subclinical but is evident as microscopic lesions in the bursa of Fabricius (Winterfield et al., 1972). This results in prolonged and severe immunosuppression which causes increased susceptibility to disease and interferes with vaccination programs against other disease agents (Allan et al., 1972). Characteristics of the disease have been reviewed in Lukert and Saif (1991) and will be summarized briefly here.

The cloacal bursa appears to be the primary target organ of the virus and birds surgically bursectomized at 4 weeks have been shown to survive a lethal IBDV challenge without clinical manifestations (Kaufer and Weis, 1980). The age of bursectomy is however, critical. Schat et al., (1981) performed embryonal bursectomy and then challenged with IBDV at 2 and 6 weeks of age. Birds developed typical hemorrhagic lesions, were clinically ill and showed some mortality. The target cells are actively dividing B lymphocytes (Muller, 1986; Burkhardt and Muller, 1987). Muller (1986) demonstrated that IBDV will replicate preferentially in lymphoid cells from the bursa and poorly in lymphoid cells from other organs. It has been proposed that clinical signs of IBDV infection may result from immune complex formation (Ley et al., 1979; Skeeles et al., 1979). Muller (1986) however, demonstrated that the preferential replication in the lymphoid cells of the bursa is not related to the presence of surface immunoglobulins.

Two serotypes of IBDV, designated 1 and 2 have been demonstrated (McFerran et al., 1980; Jackwood et al., 1984; McNulty and Saif, 1988). Virulent serotypes have been shown in Group 1. No disease has been associated with group 2 viruses. In addition, considerable antigenic variation has been documented within serotypes (Lukert and Saif, 1991).

The causative agent, IBDV, has been classified as a Birnavirus (Brown et al., 1986). The biochemistry and replication of IBDV has been reviewed in Kibenge et al., (1988). Birnaviruses are small non-enveloped animal viruses having two segments of double-stranded RNA. The smaller genomic segment (segment B) of IBDV encodes a single polypeptide of 90 k designated VP1. This protein is a minor internal component of the virion and is presumed to be the viral RNA polymerase (Hudson et al., 1986; Nagy et al., 1987; Spies et al., 1987). The larger genomic segment (segment A) encodes 5 polypeptides with the following designations and approximate molecular weights 52 k (VPX), 41 k (VP2), 32 k (VP3), 28 k (VP4) and 16 k (Azad et al., 1985). The identity and presence of the 16K polypeptide has not been confirmed (Kibenge et al., 1988). VP2, VP3 and VP4 arise by co-translational proteolytic cleavage of precursor polyproteins. The protein VP4 is thought to be a viral protease (Hudson et al., 1986) responsible for cleavage between VPX and VP4 (Duncan et al., 1987) and between VP4 and VP3 (Azad et al., 1987; Jagadish et al., 1988).

Protein VP2 is the most abundant protein of the viral capsid making up 51% of serotype I IBDV proteins (Dobos et al., 1979). VP2 is only found in mature vital particles and is not seen in IBDV infected cells (Becht et al., 1988). VP2 is thought to be a specific cleavage product of a VPX precursor. Peptide mapping has shown that VPX and VP2 of IBDV strain CU-1 have similar amino acid sequences (Muller and Becht, 1982; Dobos, 1979). In addition both VPX and VP2 react with the same monoclonal antibody on Western blots (Fahey et al., 1985b; Becht et al., 1988). It has recently been demonstrated that a conformational dependent neutralizing epitope exists on VP2 (Azad et al., 1987; Fahey et al., 1989) and a conformation independent neutralizing epitope exists on VP3 (Fahey et al., 1985 a,b). Antibodies to these epitopes were found to passively protect chickens (Fahey et al., 1985b; Azad et al., 1987; Fahey et al. 1989). Becht et al., (1988) and Snyder et al., (1988) indicated that neutralizing monoclonal antibodies to VP2 differentiated between serotypes 1 and 2 in cross-neutralization tests. However, Becht et al., (1988) also indicated that monoclonal antibodies to VP3 recognized a group-specific antigen from both serotypes which was not associated with neutralizing activity or protection. These studies may indicate the existence of multiple epitopes at least on VP2 and perhaps on VP3.

In a recent publication, Macreadie et al., (1990) demonstrated the expression of VP2 in a yeast vector. The size of the expressed protein was consistent with that of an authentic VP2. Centrifugation and gel filtration studies indicated that the VP2 expressed in yeast was in a high molecular weight aggregated form. Chickens inoculated with a crude extract of the yeast expressed VP2 developed an immune response as demonstrated by ELISA test and virus neutralization tests. One day old chickens were then inoculated with anti-sera from chickens previously inoculated with yeast expressed VP2. These chickens were passively protected against IBDV challenge as evidenced by lack of IBDV antigen in the bursa (Macreadie et al., 1990).

Current vaccination strategies against IBDV include both live and killed vaccines. Antibody transmitted from the hen via the yolk of the egg can protect chickens against early infections with IBDV. Therefore, use of killed vaccines in oil emulsions to stimulate high levels of maternal antibody is extensive in the field (Lukert and Saif, 1991). Studies by Lucio and Hitchner (1979) and Baxendale and Lutticken (1981) indicated that oil emulsion IBDV vaccines can stimulate adequate maternal immunity to protect chickens for 4–6 weeks. In contrast progeny from breeders vaccinated with live vaccines are protected for only 1–3 weeks after hatching (Lukert and Saif, 1991).

Determination of when maternal antibody has waned, and thus when antibody levels can be boosted by active immunization is problematical. It is therefore common practice to vaccinate all chicks against IBD with a live vaccine during the first 3 weeks of life (Winterfield et al., 1980). Inactivated vaccines are ineffective in inducing active immunity in chicks with maternal antibody. Presently available live vaccines consist of strains of intermediate virulence or highly attenuated strains, as well as some cell culture adapted variant strains. While intermediate strains can break through maternal antibody titers of approximately 1:250 (Lukert and Saif, 1991), the strains vary in virulence and can induce bursal atrophy and immunosuppression in day old and 3 week old SPF chickens (Lukert and Mazariegos, 1985).

Given the limitations of current vaccination strategies, it can be appreciated that provision of an IBDV recombinant poxvirus, and of vaccines which provide protective immunity against IBDV infections, would be a highly desirable advance over the current state of technology.

OBJECTS OF THE INVENTION

It is therefore an object of this invention to provide recombinant poxviruses, which viruses express gene products of IBDV, and to provide a method of making such recombinant poxviruses.

It is an additional object of this invention to provide for the cloning and expression of IBDV coding sequences, particularly sequences coding for IBDV structural proteins, in a poxvirus vector, particularly fowlpox virus.

It is another object of this invention to provide a vaccine which is capable of eliciting IBDV antibodies and protective immunity against IBDV infection.

These and other objects and advantages of the present invention will become more readily apparent after consideration of the following.

STATEMENT OF THE INVENTION

In one aspect, the present invention relates to a recombinant poxvirus containing therein a DNA sequence from IBDV in a nonessential region of the poxvirus genome. The poxvirus is advantageously an avipox virus, such as fowlpox virus.

According to the present invention, the recombinant poxvirus expresses gene products of the foreign IBDV gene. In particular, the foreign DNA codes for IBDV structural proteins. The IBDV gene may be co-expressed with other foreign genes in the host by the recombinant poxvirus.

In another aspect, the present invention relates to a vaccine for inducing an immunological response in a host animal inoculated with the vaccine, said vaccine including a carrier and a recombinant poxvirus containing, in a nonessential region thereof, DNA from IBDV. Advantageously, the DNA codes for and expresses IBDV structural proteins. The IBDV gene may be co-expressed with other foreign genes in the host. The poxvirus used in the vaccine according to the present invention is advantageously an avipox virus, such as fowlpox virus, referred to hereafter as TROVAC.

BRIEF DESCRIPTION OF THE DRAWINGS

A better understanding of the present invention will be had by referring to the accompanying drawings, in which:

Cell Lines and Virus Strains. The strain of FPV designated FP-1 has been previously described (Taylor et al., 1988). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast (CEF) cells. This virus was obtained in September 1980 by Rhone Merieux, Lyon, France and a master viral seed established. Subsequently, the virus was subjected to four successive plaque purifications. One plaque isolate was further amplified in primary CEF cells, and a stock virus, designated as TROVAC, established.

cDNA clones from IBDV strain Faragher (Type I) were obtained from Rhone Merieux, Lyon, France.

EXAMPLE 1

CONSTRUCTION OF INSERTION VECTOR FOR IBDV-VP2

Plasmid pIBDVA contains a 3.1 Kb KpnI to XbaI fragment derived from cDNA clones of IBDV strain Faragher. This fragment was inserted into vector pBluescript II SK+ (Stratagene, La Jolla, Calif.). The insert corresponds to the segment A of the IBDV genome which encodes the 108 kDa precursor polyprotein. The polyprotein is subsequently processed to form VP2, VP3 and VP4.

In order to isolate the coding sequence for VP2 from pIBDVA, VP3 and VP4 coding sequences were deleted from pIBDVA and a termination codon added to the 3' end of the VP2 coding sequence. This was accomplished by digestion of pIBDVA with ScaI and KpnI and insertion of the annealed and kinased oligonucleotides CE279 (SEQ ID NO: 1) and CE280 (SEQ ID NO: 2) to form pCEN112.

```
CE279  ACTTCATGGAGGTGGCCGACCTCAACTCTCCCCTGAAGATTGCAGGAGCATTTGG
       CTTCAAAGACATAATCCGGGCTATAAGGAGGTGAGTCGACGGTAC
CE280  CGTCGACTCACCTCCTTATAGCCCGGATTATGTCTTTGAAGCCAAATGCTCCTGC
       AATCTTCAGGGGAGAGTTGAGGTCGGCCACCTCCATGAAGT
```

FIG. 1 (SEQ ID NO: 7) shows the nucleotide sequence of a 3661 base pair fragment of TROVAC DNA containing the F8 open reading frame; and FIG. 2 (SEQ ID NO: 12) shows the nucleotide sequence of a 3659 base pair fragment of TROVAC DNA containing the F8 open reading frame.

DETAILED DESCRIPTION OF THE INVENTION

The invention is directed to recombinant poxviruses containing therein a DNA sequence from IBDV in a nonessential region of the poxvirus genome. The recombinant poxviruses express gene products of the foreign IBDV gene. In particular, IBDV genes encoding IBDV structural proteins were isolated, characterized and inserted into TROVAC (FPV) recombinants.

The vaccinia virus H6 promoter previously described in Taylor et al., (1988); Guo et al., (1989), Perkus et al., (1989), was inserted into pCEN112 by digesting pCEN112 with NotI, and blunt-ending with the Klenow fragment of DNA polymerase, in the presence of 10 mM dNTPs. A HindIII to EcoRV fragment which contains the H6 promoter was blunt-ended with the Klenow fragment of DNA polymerase and inserted into the linearized pCEN112 to generate pCEN117.

In order to couple the promoter sequence with the initiating ATG of IBDV VP2 coding sequence, the annealed and kinased oligonucleotides CE277 (SEQ ID NO: 3) and CE278 (SEQ ID NO: 4) were inserted into pCEN117 that had been digested with NruI and RsrII. The resulting plasmid was designated pCEN120.

```
CE277  CGATATCATGACAAACCTGCAAGATCAAACCCAACAGATTGTTCCGTTCATACGG
       AGCCTTCTGATGCCAACAACCG
```

| CE278 | GTCCGGTTGTTGGCATCAGAAGGCTCCGTATGAACGGAACAATCTGTTGGGTTTG ATCTTGCAGGTTTGTCATGATATCG |

A SmaI to SalI fragment from pCEN120, containing IBDV-VP2 linked to the vaccinia virus H6 promoter was cloned into the HpaI and SalI sites of the FPV insertion vector pCEN100 (described below) to generate pCEN137. Plasmid pCEN137 was used in an in vitro recombination test to generate recombinant vFP115.

EXAMPLE 2

CONSTRUCTION OF INSERTION VECTOR FOR IBDV VP2, VP3, VP4

Non-coding sequence was removed from the 3' end of the IBDV polyprotein sequence by partially digesting pIBDVA with PpuMI, completely digesting with KpnI, and re-inserting the annealed and kinased oligonucleotides CE275 (SEQ ID NO: 5) and CE276 (SEQ ID NO: 6) into pIBDVA to generate pCEN111.

| CE275: | GACCTTGAGTGAGTCGACGGTAC |
| CE276: | CGTCGACTCACTCAAG |

A perfect 5' end to the polyprotein sequence was obtained in the following manner. A KpnI-BstEII fragment containing the majority of the polyprotein sequence with a perfect 3' end was excised from pCEN111 and ligated into the KpnI and BstEII sites of pCEN120. This substitution replaces the 3' end of the VP2 coding sequence and generates a perfect 5' end for the polyprotein with linkage to the vaccinia virus H6 promoter. The resulting plasmid was designated pCEN125. The final insertion plasmid was constructed by partial digestion of pCEN125 with SmaI and complete digestion with SalI. The resulting fragment was cloned into the HpaI and SalI sites of pCEN100 (described below) to form pCEN138. Plasmid pCEN138 was used in an in vitro recombination test to generate recombinant vFP116.

(SEQ ID NO: 7). The limits of an open reading frame designated in this laboratory as F8 were determined within this sequence.

Subsequently, the nucleotide sequence of FIG. 1 was further analyzed and was determined on both strands to be a 3659 bp PvuII-EcoRV fragment. This sequence is shown in FIG. 2 (SEQ ID NO: 12). The limits of the open reading frame designated in this laboratory as F8 were determined within this sequence; and, the subsequent determination of the sequence, as shown in FIG. 2, does not affect the reproducibility of this or any other construction involving the fowlpox F8 locus determined by this laboratory, especially because the deletions and insertions into the F8 ORF can be performed by the skilled artisan following the teachings from this laboratory, such as the following description, without recourse to the sequence of the F8 ORF or the PvuII-EcoRV fragment within which it is contained. Based on sequence information contained in FIG. 2, the open reading frame is initiated at position 495 and terminates at position 1887. A deletion was engineered from what was ultimately determined to be position 779 to position 1926, as described below.

Plasmid pRW761 is a sub-clone of pRW731.15 containing a 2430 bp EcoRV-EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO: 8) and JCA018 (SEQ ID NO: 9).

| JCA017 | 5' CTAGACACTTTATGTTTTTTAATATCCGGTCTTAAAAGCTTCCCGGGGGA TCCTTATACGCGGAATAAT 3' |
| JCA018 | 5' ATTATTCCCCGTATAAGGATCCCCCGGGAAGCTTTTAAGACCGGATATTA AAAAACATAAAGTGT 3' |

The plasmid resulting from this ligation was designated pJCA002.

Additional cloning sites were incorporated into pJCA002 by inserting the annealed and kinased oligonucleotides CE205 (SEQ ID NO: 10) and CE206 (SEQ ID NO: 11) into the BamHI and HindIII sites of pJCA002 to form pCE72.

| CE205: | GATCAGAAAAACTAGCTAGCTAGTACGTAGTTAACGTCGACCTGCAGAAG CTTCTAGCTAGCTAGTTTTTAT |
| CE206: | AGCTATAAAAACTAGCTAGCTAGAAGCTTCTGCAGGTCGACGTTAACTAC GTACTAGCTAGCTAGTTTTTCT |

EXAMPLE 3

CONSTRUCTION OF FOWLPOX INSERTION PLASMID AT F8 LOCUS

Plasmid pRW731.15 contains a 10 Kbp PvuII-PvuII fragment cloned from TROVAC genomic DNA. The nucleotide sequence was determined on both strands for a 3661 bp PvuII-EcoRV fragment. This sequence is shown in FIG. 1

In order to increase the length of the FPV flanking arms in the insertion plasmid, plasmid pJCA021 was constructed. Plasmid pJCA021 was obtained by inserting a 4900 bp PvuII-HindII fragment from pRW731.15 (described above) into the SmaI and HindII sites of pBluescript SK+ (Stratagene, La Jolla, Calif.). A BglII to EcoRI fragment from pCEN72 was then ligated into the BglII and EcoRI sites of pJCA021 to generate pCEN100.

EXAMPLE 4

DEVELOPMENT OF TROVAC-IBDV RECOMBINANTS

Plasmids pCEN137 and pCEN138 were transfected into TROVAC infected primary CEF cells by using the calcium phosphate precipitation method previously described (Panicali and Paoletti, 1982; Piccini et al., 1987). Positive plaques were selected on the basis of hybridization to specific IBDV radiolabeled probes and subjected to five sequential rounds of plaque purification until a pure population was achieved. One representative plaque from each IVR was then amplified and the resulting TROVAC recombinants were designated vFP115 (IBDV-VP2) and vFP116 (IBDV-VP2, VP3, VP4).

Immunofluorescence. In order to determine where the IBDV proteins were localized in recombinant infected CEF cells, immunofluorescence analysis was performed. Indirect immunofluorescence was performed was performed as described in Taylor et al., (1990) using a neutralizing monoclonal antibody preparation specific for VP2 and designated AC6 and and a VP3 specific monoclonal antibody designated NA3 obtained from Rhone Merieux. In addition, a polyclonal chicken anti-IBDV serum was obtained from Spafas Inc., Storrs, Conn.

The results indicated that IBDV specific immunofluorescence could be detected in the cytoplasm of cells infected with either vFP115 or vFP116. No fluorescence was detected in parental TROVAC infected CEF cells. No surface fluorescence was detected in cells infected with either recombinant virus. Equivalent results were obtained using both the neutralizing monoclonal antibody preparation and the polyclonal immune serum. The result was not unexpected since the analysis of the sequence of the IBDV genes does not indicate the presence of characteristic signal and anchor sequences which would direct insertion of the proteins in the infected cell membrane.

Immunoprecipitation. Immunoprecipitation reactions were performed as described in Taylor et al., (1990) using the monoclonal antibody preparations and the polyclonal anti-IBDV immune serum from chickens as described above.

Immunoprecipitation analysis of CEF cells infected with recombinant vFP115 indicated the expression of a protein of approximately 38–40 Kd recognized by both polyclonal immune sera and the neutralizing monoclonal antibody. This size is appropriate for expression of the structural protein, VP2 (Azad et al., 1985). Immunoprecipitation analysis of lysates of cells infected with recombinant vFP116 encoding the IBDV polyprotein, with the same serological reagents, also demonstrated expression of a single protein species of approximately 43 kd. This protein is recognized by both polyclonal immune serum and the neutralizing monoclonal antibody preparation. Both the size of the protein and its recognition by the monoclonal antibody indicate that the identity of this protein may be VPX, the precursor to VP2. Although no other proteins are immunoprecipitated by the polyclonal immune serum, presence of the cleaved VPX indicates that VP4, the cleavage protein is probably expressed. Since VP4 is a very minor component of the virion, it is not unusual that the immune serum should not contain antibodies to this protein. Use of the VP3 specific monoclonal antibody indicated the expression of a protein of 32 kd in cells infected with vFP116.

EXAMPLE 5

IMMUNIZATION OF CHICKENS AND SUBSEQUENT CHALLENGE

Groups of 20, 5 day old susceptible SPF chickens were inoculated by subcutaneous injection in the nape of the neck with 0.2 ml of recombinants vFP115 or vFP116. This corresponded to a dose of approximately 4.0 $\log_{10}$ TCID$_{50}$. A group of 19 birds were left as uninoculated controls. At fourteen days post vaccination, chickens were bled and serum neutralizing titers in the sera were determined. Birds were challenged at 14 days by intra-ocular inoculation of 0.03 ml of the virulent heterologous serotype I IBDV challenge strain (designated STC) supplied by the USDA National Veterinary Services Laboratory. Five days after challenge, each chicken was necropsied and the bursa examined for gross lesions and the appearance of atrophy. The results are shown in Table 1.

The results indicate that inoculation of one dose of vFP115 expressing the VP2 structural protein leads to the induction of serum neutralizing antibody and 75% protection of challenged birds. Inoculation of vFP116 leads to the induction of a poor neutralizing antibody response but 50% of challenged birds are protected.

TABLE 1

Protective Efficacy of TROVAC-IBDV Recombinants in Chickens

| Recombinant | # Protected/Challenged[b] | % Protection | SN Titer[a] |
| --- | --- | --- | --- |
| vFP115 | 15/20 | 75 | 131 |
| vFP116 | 10/19 | 53 | 6 |
| Controls | 0/19 | 0 | 0 |

[a]Serum neutralization titer
[b]Birds are considered protected in the absence of bursal atrophy and lesions.

EXAMPLE 6

IBDV RECOMBINANT POXVIRUS VACCINES

Recombinant poxviruses containing, in a nonessential region thereof, DNA from IBDV provide advantages as vaccines for inducing an immunological response in a host animal. Infectious bursal disease virus is very stable and persists in the environment for long periods. For economic reasons, poultry houses are rarely cleaned between broods and thus chickens are exposed to the virus early in life. Since elimination of virus by hygienic means is not possible, vaccination strategies need to be formed. Active immunization of chickens is difficult in the presence of maternal antibody. In addition, since maternal antibody levels are variable and the rate of loss of antibody unpredictable, timing of vaccination is a problem. A successful vaccine will need to be able to boost immunity in the presence of maternal antibody and should also contain cross-reactive antigens from a number of different serotypes. In addition, an effective vaccine should not induce signs of disease in vaccinated birds.

TROVAC-IBDV recombinant vFP115 expressed the major structural protein VP2 which has been shown to contain at least one highly immunogenic region. The protein expressed by the TROVAC recombinant is recognizable by IBDV immune serum. Inoculation of this recombinant into susceptible birds resulted in 75% protection from bursal damage. Recombinant vFP116 contains the coding sequence for the polyprotein VP2, VP3, VP4. A protein probably corresponding to VPX, the VP2 precursor, was expressed which is also recognized by IBDV immune sera. Inoculation of this recombinant into susceptible birds lead to the development of low neutralizing antibody levels, but induced 53% protection from bursal damage.

The results indicate the potential of TROVAC-IBDV recombinants for vaccination against IBDV in the poultry industry. The restricted host range of FPV provides an inherent safety barrier to transmission of recombinant to non-vaccinated species. Use of antigenic regions of IBDV rather than whole virus eliminates the need to introduce live virus to the environment and may lessen the immunological pressure on the virus which leads to the emergence of variant strains. The large size of the FPV genome allows incorporation of multiple antigenic sequences and should allow for vaccination against a variety of strains.

EXAMPLE 7

FURTHER IMMUNOGENICITY AND EFFICACY STUDIES WITH vFP115

Effect of dose of inoculation on protective efficacy induced by vFP115. Groups of day old SPF chickens were inoculated with vFP115 by the subcutaneous route in the nape of the neck. The virus was administered in doses of 4.9, 5.5 or 6.2 $\log_{10}$ EID$_{50}$ per bird. At 21 days post-vaccination, ten vaccinates and ten naive birds were bled and the sera analyzed for the presence of IBDV specific serum neutralizing (SN) antibody. At 28 days, birds were challenged by administration by the ocular route of 1.3 $\log_{10}$ EID$_{50}$ of the heterologous Standard Challenge Strain of IBDV. At 5 days post-challenge, 5 birds from each group were necropsied and bursae examined for gross lesions. At 11 days post-challenge, the remaining birds were killed and bursa to body weight ratios determined. The results of analysis are shown in Table 2. The results indicate that increasing the inoculation dose has led to the induction of slightly higher levels of SN antibody, but that the protective efficacy is not enhanced. Birds were considered protected when the bursa to body weight ratio after challenge was greater than one standard deviation of the mean bursa to body weight ratio of infected control birds. Using this criteria, and considering bursa to body weight ratios of individual birds, protection ratios of 65%, 74% and 64% were obtained for vFP115 dosages of 4.9, 5.5 and 6.2 $\log_{10}$ EID$_{50}$ respectively.

TABLE 2

Dose Response Study of Inoculation of vFP115 in Day Old Chickens

| Dose | SN GMT[a] | Bursal Lesions[b] Positive/Total | Bursa/Body Weight Ratio[c] |
|---|---|---|---|
| 4.9 | 13 | 1/5 | 3.5 |
| 5.5 | 35 | 2/5 | 3.2 |
| 6.2 | 102 | 1/5 | 3.2 |
| Control | 0 | 5/5 | 1.6 |

[a]Geometric Mean Titer of sera of 10 birds
[b]Bursa of 5 birds examined for gross lesions
[c]Ratio expressed as a mean of 23 birds Effect of Age of Bird on Protective Efficacy of vFP115. Groups of 30 one-, four-, seven- and fourteen day old SPF birds were inoculated by the subcutaneous route with 4.0 $\log_{10}$ EID$_{50}$ of vFP115. At 21 days post-vaccination, 10 vaccinates and 5 naive controls of each group were bled and sera analyzed for the presence of SN antibody. At 28 days post-vaccination, all vaccinates and naive controls were challenged by the ocular route with 1.3 $\log_{10}$ EID$_{50}$ of the heterologous STC virus strain. Four days post-challenge, birds were sacrificed and bursa examined for evidence of bursal damage. The results of analysis are shown in Table 3. The results indicate that while IBD specific SN titers and protection after challenge are obtained at one day of age, when vaccination is delayed past 4 days of age higher SN titers are obtained and the level of protection is increased.

TABLE 3

Effect of Age of Bird on Protective Efficacy of vFP115

| Age Group | Treatment | GMT | Protection Ratio | % Protection |
|---|---|---|---|---|
| 1 day | Vaccinates | 126 | 23/30 | 77 |
|  | Controls |  | 0/10 | 0 |
| 4 days | Vaccinates | 666 | 25/30 | 83 |
|  | Controls |  | 0/10 | 0 |
| 7 days | Vaccinates | 1946 | 29/30 | 97 |
|  | Controls |  | 1/10 | 0 |
| 14 days | Vaccinates | 1408 | 30/30 | 100 |
|  | Controls |  | 0/10 | 0 |

Effect of route of inoculation on induction of a protective immune response by vFP115. Groups of twenty 14 day old SPF birds were inoculated by (a) the intramuscular route in the leg, (b) ocular route or (c) oral route with 4.0 $\log_{10}$ TCID$_{50}$ of vFP115. At 14 and 28 days post-inoculation sera were collected and analyzed for the presence of IBDV specific SN antibody. At both 14 and 28 days post-vaccination, groups of birds were challenged by ocular inoculation of 2.5 $\log_{10}$ EID$_{50}$ of the homologous Faragher strain of IBDV. Deaths were recorded and at 4 days post-challenge all birds were sacrificed and Bursa examined for the presence of macroscopic lesions. Significant neutralizing antibody responses were found only after inoculation of vFP115 by the intramuscular route with SN titers of approximately 2.0 $\log_{10}$ at 14 and 28 days post-inoculation. By ocular and oral routes, low SN titers were achieved in 30 and 10% of chickens, respectively. The results of challenge are shown in Table 4. All birds inoculated with vFP115 by the intramuscular route were fully protected from challenge which was pathogenic in all control non-vaccinated birds at 14 and 28 days post-inoculation. No protection was observed following the oral route of inoculation. Partial protection was seen by the ocular route.

TABLE 4

Effect of Route of Inoculation on Protective Efficacy Induced By vFP115

| Route of Inoculation | % Protection from challenge at | |
|---|---|---|
|  | 14 days post-vacc | 28 days post-vacc |
| Intramuscular | 100 | 100 |
| Ocular | 50 | 10 |
| Oral | 0 | 0 |

EXAMPLE 8

DEVELOPMENT OF A TROVAC RECOMBINANT EXPRESSING THE VP3 STRUCTURAL PROTEIN

Example 2 describes the development of a TROVAC based recombinant vFP116 expressing the VP2, VP4, VP3 polyprotein. Efficacy studies described in Example 5 indicate that this recombinant induces lower levels of protection than vFP115 expressing the VP2 protein after inoculation into susceptible chickens. In vitro studies showed that the VP2 protein expressed in the vFP116 construct is slightly larger than that expressed in the vFP115 construct and that expression of the VP3 protein is not detectable by a polyclonal serum. Immunofluorescence and immunoprecipitation analysis with a VP3 specific monoclonal antibody, however, indicated that the VP3 protein is expressed in vFP116. In order to evaluate the role of the VP3 protein in eliciting cross-protective immunity, a single recombinant was developed expressing the VP3 protein from the Faragher strain of IBDV.

Construction of a Fowlpox Insertion Plasmid at the F16 Locus. The plasmid pFP23K (described by Tartaglia et al., 1990) contains a 10.5 kb HindIII fragment from the fowlpox (FP) genome. A 7.3 kb NaeI\NdeI FP fragment was isolated from pFP23K and ligated to a similarly cut pUC9 vector to generate pRW866. A unique FspI site within this FP fragment lies between two ORFs (intergenic region) and is the F16 insertion locus.

In order to create a multiple cloning site (MCS) cassette for the F16 locus, two PCR fragments were amplified from pFP23K using primers RW264 (SEQ ID NO: 13) plus RW265 (SEQ ID NO: 14) and RW266 (SEQ ID NO: 15) plus RW267 (SEQ ID NO: 16). The resulting fragments were mixed together and amplified with primers RW266 and RW267 which resulted in a single, fused fragment. This fragment was digested with EcoRI and NdeI and ligated into similarly cut pRW715 (derived from pUC9 by digesting with PvuII and ligating an EcoRI linker between the two pvuII sites), to yield pRW864. The MCS cassette consists of a polycloning region (SmaI-BamHI-HindIII sites) flanked on either side by translational stop codons in all six reading frames and a NotI site. A vaccinia early transcriptional stop signal is located on the HindIII end.

resulting in pRW868. The lacZ gene from pRW868 was excised using NotI and replaced with the MCS cassette derived as a NotI fragment from pRW864 resulting in pRW873, the F16 insertion plasmid.

Development of an FP recombinant expressing VP3. The complete IBDV VP3 ORF was excised from pCEN111 (described in Example 3) as a 1262 bp BamHI and Asp718 fragment and ligated into a similarly cut pSD554VC (a vaccinia donor plasmid containing the H6 promoter) to yield pFT1. A 112 bp PCR fragment was amplified from pCEN111 using oligonucleotides JP003 (SEQ ID NO: 17) and JP004 (SEQ ID NO: 18), digested with NruI/ScaI, and gel purified. This fragment was ligated into pFT1 digested completely with NruI and partially with ScaI to yield pIBDV-VP3II. This plasmid contains the vaccinia H6 promoter coupled to the VP3 ORF.

A PCR fragment was amplified from pRW823 which contains vaccinia virus H6 promoter sequences using oligonucleotides RG662 (SEQ ID NO: 19) and RG663 (SEQ ID NO: 20). This fragment was digested with HindIII/SmaI and ligated into the F16 insertion plasmid (pRW873) cut with the same enzymes resulting in pF16VQH6. A cassette containing part of the H6 promoter fused to the VP3 ORF was excised from pIBDV-VP3II with NruI/Asp718, the ends repaired with Klenow polymerase, and the purified fragment ligated into pF16VQH6 cut with NruI/SmaI to generate the donor plasmid pF16VP3F.

RW264: AATTAACCCGGGATCCAAGCTTCTAGCTAGCTAATTTTT
ATAGCGGCCGCTATAATCGTTAACTTATTAG
RW265: CTAGCTAGAAGCTTGGATCCCGGGTTAATTAATTAATAAAAA
GCGGCCGCGTTAAAGTAGAAAAATG
RW266: GTTACATATGTACAGAATCTGATCATAG
RW267: GCTAGAATTCTCTTAGTTTTTATAGTTG

The following describes a series of plasmid constructs which ultimately leads to the MCS cassette from pRW864

JP003    5'-AAGGTAGTACTGGCGTCC-3'
JP004    5'-TTATCGCGATATCCGTTAAGTTTGTATCGTAATATGTTCCCTCACAATC-
         CACGA-3'
RG662    5'-TAAAAGCTTTTAATTAATTAGTCATC-3'
RG663    5'-TAACCCGGGCGATACAAACTTAACGG-3' being inserted into the FspI site of pRW866 to generate the F16 insertion plasmid (pRW873). A cassette containing the E. coli lacZ gene coupled to the vaccinia 11K promoter was excised from pAM1BG as a BamHI/PstI fragment. Plasmid pAM1BG contains the lacZ BamHI fragment from pMC1871 (Casadaban et al., 1983) inserted in the previously described BamHI site 3' of the 11K vaccinia virus promoter (Paoletti et al., 1984). The ends were repaired using Klenow polymerase and the cassette ligated into pRW864 cut with SmaI to yield pRW867A. The lacZ gene cassette was excised from pRW867A using NotI and the ends repaired with Klenow polymerase. This fragment was then ligated into the unique FspI site in the FP sequences of pRW866

Plasmid pF16VP3F was used in in vitro recombination with TROVAC as the rescuing virus to derive recombinant vFP186. Immunoprecipitation analysis using a VP3 specific monoclonal antibody has confirmed the expression of a protein of approximately 32 kd in CEF cells infected with the recombinant.

EXAMPLE 9

DEVELOPMENT OF TROVAC BAAED RECOMBINANTS WITH ALTERED MODES OF EXPRESSION OF THE VP2 PROTEIN

It has been postulated that a protein displayed on the infected cell surface may lead to a more efficient induction of neutralizing antibody than if the protein is secreted or expressed internally. Previous studies have indicated that expression of a foreign antigen on the infected cell surface by a recombinant vaccinia virus, can be achieved by recombinant DNA techniques by adding appropriate signal and anchor sequences (Langford et al., 1986; Vijaya et al., 1988). The VP2 protein in IBDV infected cells is not a membrane bound glycoprotein and possesses neither an endogenous signal nor anchor sequences. A strategy was devised to add the appropriate signal and anchor sequences from the Newcastle Disease Virus fusion protein. The fusion protein is an integral membrane bound glycoprotein. This strategy is described below.

The IBDV VP2 ORF plus translational stop codon was excised from pCEN112 (described in Example 1) as an XbaI/SalI fragment and the ends repaired using Klenow polymerase. This cassette was ligated into the HincII site of pUC18 to generate pCE147. The vaccinia H6 promoter coupled to the NDV fusion gene signal sequence was obtained by isolating a HindIII/PstI fragment from pCE64 (for complete NDV Fusion sequences see Taylor et al., 1990). This fragment contains the H6 promoter fused to the first 25 codons from the N-terminus of the NDV fusion ORF. This fragment was ligated into pCE147 cut with HindIII/PstI to yield pCEN150.

In order to couple the last codon from the NDV fusion signal sequence with the first codon from the VP2 ORF, a PCR fragment was amplified from pCEN150 using oligonucleotides CE329 (SEQ ID NO: 21) and CE330 (SEQ ID NO: 22) as primers. The fragment was digested with KpnI/RsrII and ligated into pCEN150 cut with the same enzymes to generate pCEN156. The H6 promoted-NDV fusion signal sequence-VP2 ORF cassette was excised from pCEN156 with HindIII/EcoRI, the ends repaired using Klenow polymerase, and the cassette ligated into pCEN100 (the F8 insertion plasmid) cut with HpaI to generate the donor plasmid pIBDV-VP2-SS.

fluid. This result is in keeping with the addition of a signal sequence to the coding sequence of the VP2 protein. In vitro recombination using plasmid pIBDV-VP2-SSA and TROVAC as the rescuing virus generated recombinant vFP151. Expression analysis using both polyclonal immune serum and the VP2 specific monoclonal antibody indicated that the VP2 protein is expressed at the infected cell surface as expected following the addition of an anchor sequence. The fact that the VP2 protein is still recognized by the monoclonal antibody in this form of presentation indicates that conformation of this particular epitope has not been altered by the manipulations.

Efficacy studies were performed by inoculating day-old SPF chickens with $4.0 \log_{10} TCID_{50}$ of each recombinant. At 28 days birds were challenged by ocular inoculation of the heterologous STC challenge strain. In contrast to previous results obtained with the unmodified VP2 expressed in vFP115, no protection was obtained after vaccination with either vFP147 or vFP151. Further in vitro studies using tunicamycin, an inhibitor of N-linked glycosylation, have indicated that the modified VP2 proteins expressed by both vFP147 and vFP151 are glycosylated whereas the unmodified VP2 expressed in vFP115 is not. It is postulated that the addition of sugar moieties to the VP2 protein may alter conformation of the protein in areas apart from the neutralizing epitope. Alternatively, the addition of the signal and anchor sequences as constructed here, may alter conformation of the protein. In either case it appears that the antibody induced by the modified constructions is not able to neutralize the heterologous challenge virus (STC). However, vFP147 and vFP151 and products therefrom are nonetheless useful. The modified VP2 expressed by these recombinants can be used as precursors to generate the VP2 protein; for example, by removal of the additional sugar moieties or to isolate secreted VP2 protein from tissue culture supernatant for further purification.

EXAMPLE 10
DEVELOPMENT OF POXVIRUS RECOMBINANTS EXPRESSING THE VP2 PROTEIN FROM HETEROLOGOUS STRAINS OF IBDV

```
CE329  5'-GATCCCGGTACCTCTAATGCTGATCATCCGAACCGCGCTGACACTG-
       AGCTGTACAAACCTGCAAGATCAAAC-3'
CE330  5'-GGACGCCGGTCCGGTTGTTGGCATC-3'
```

To add the NDV fusion transmembrane sequences to the above plasmid, a 240 bp PCR fragment was amplified from pIBDV-VP2-SS using primers RG583 (SEQ ID NO: 23) and RG590 (SEQ ID NO: 24). This fragment contains 49 codons plus stop codon from the C-terminus of the NDV fusion ORF (see Taylor et al., 1990). The purified fragment was digested with ScaI/BamHI and ligated into pIBDV-VP2-SS cut completely with BamHI and partially with ScaI to generate the donor plasmid pIBDV-VP2-SSA.

IBDV strains show considerable variation in their ability to cross-neutralize. Sequence analysis of different strains has shown that one critical region involved in virus neutralization resides within a conformational epitope located on VP2. Sequence information for VP2 is available for the Faragher (Bayliss et al., 1990) and STC (Kibenge et al., 1990) strains and it has been determined that five amino acid differences between the two strains occur within the conformational epitope. A strategy was therefore devised to alter the coding

```
RG583  5'-GTGAGTACTTCATGGAGGTGGCCGACCTCAACTCTCCCCTGAAGA-
       TTGCAGGAGCATTTGGCTTCAAAGACATAATCCGGGCTATAAGGA-
       GGATCGTTTTAACTGTCATATC-3'
RG590  5'-TTAGGATCCTCATATTTTTGTAGTGGCTCTC-3'
```

In vitro recombination using plasmid pIBDV-VP2-SS and TROVAC as the rescuing virus generated recombinant vFP147. Expression analysis of this recombinant with both polyclonal immune serum and a VP2 specific monoclonal antibody indicated that the VP2 protein is expressed internally, and in addition is secreted into the tissue culture sequence of the Faragher strain conformational epitope to conform with the sequence of the STC strain. This procedure is described below.

Mutagenesis of VP2 Faragher to VP2 STC. In order to change the VP2 Faragher sequence in pCEN120 (described in Example 1) to the VP2 STC sequence, five codons were changed in the VP2 ORF using PCR site directed mutagenesis (see Kibenge et al., 1990 for STC sequence). Oligonucleotide primers RG677 (SEQ ID NO: 25) plus RG678 (SEQ ID NO: 26) and RG685 (SEQ ID NO: 27) plus RG686P (SEQ ID NO: 28) were used to amplify a 530 bp and a 270 bp fragment respectively from pCEN100

| | |
|---|---|
| RG714 | 5'-AACATATTTCCGAACAG-3' |
| RG715 | 5'-TCCAAGCTTTCGCGACCCGGGTTTTTATTAGCTAATTAGCAATAT-AGATTCAATATG-3' |
| RG716 | 5'-ATCAAGCTTGGATCCCTCGAGTTTTTATTGACTAGTTAATCATAA-GATAAATAATATACAGC-3' |
| RG717 | 5'-GATATAGAAGATACCAG-3' |

(described in Example 3). The gel purified 270 bp fragment was further amplified using oligonucleotides RG702 (SEQ ID NO: 29) and RG704 (SEQ ID NO: 30). The 530 bp fragment was digested with SacI and partially digested with PstI. The 270 bp fragment was digested with SacI and NcoI. These purified PCR amplified fragments, which contain the five STC codon changes, were ligated into pCEN120 cut with PstI and NcoI. The resulting plasmid, pVP2-STC was confirmed by DNA sequencing analysis.

| | |
|---|---|
| RG677 | 5'-TACACACTGCAGAGCAATGGGAACCTCAAGTTCGATCAGATG-3' |
| RG678 | 5'-GAAACACGAGCTCTCCCCCAACGCTGAGGCTTGTGATAG-3' |
| RG685 | 5'-GGAAGAGCTCGTGTTTCAAACAAGCGTCCAAGGCCTTGTACTGGG-CGCCACCATCTACTTTATAGGCTTTGATGGGACTACGGTAATCAC-CAGAGCTGTAGCCGCAGATAATGGGCTGACGGCCGGCACCGACAA-TCTTATGCCATTCAATCTTG-3' |
| RG686P | 5'-CCACCATGGATCGTCACTGCTAGGCTCCCACTTGCCGACCATGAC-ATCTGATCCCCTGCCTGACCACCACTTTTGGAGGTCACTACCTCC-AGTTTGATGGATGTGATTGGCTGGGTTATCTCATTGGTTGGAATG-ACAAGATTGAATGGCATAAG-3' |
| RG702 | 5'-GGGAGAGCTCGTGTTTCAAACAAGCG-3' |
| RG704 | 5'-CCACCATGGATCGTCACTGC-3' |

Construction of the new F8 insertion plasmid. In order to remove all of F8 coding sequences from the original F8 insertion plasmid (pCEN100), a new F8 insertion plasmid was constructed. pJCA021 contains a 4900 bp PvuII/HincII fragment from TROVAC which includes the F8 gene and flanking sequences. A 4.2 kb NciI/PpuMI fragment was isolated from this plasmid and the ends repaired with Klenow polymerase. This fragment was ligated into pBluescript SK+ cut with XbaI/Asp718 and repaired with Klenow polymerase to yield pIY.

The strategy to delete the F8 ORF from pIY and replace it with a multiple cloning site (MCS) used PCR amplification of two fragments from pJCA021 with oligonucleotide primers containing the multiple cloning sequences. A 335 bp fragment was amplified from pJCA021 using oligonucleotides RG714 (SEQ ID NO: 31) and RG715 (SEQ ID NO: 32) and digested with HindIII and EcoRI. Similarly, a 465 bp fragment was amplified from pJCA021 using oligonucleotides RG716 (SEQ ID NO: 33) and RG717 (SEQ ID NO: 34) and digested with HindIII and BglII. The two PCR fragments were ligated into pIY cut with EcoRI and BglII in a three fragment ligation resulting in pF8. This plasmid is the new F8 insertion plasmid which contains a MCS consisting of SmaI, NruI, HindIII, BamHI and XhoI sites flanked by vaccinia early transcriptional stop signals and translational stops in all six frames. The length of the left arm is about 1430 bp and the length of the right arm is about 1380 bp. The F8 gene ORF which initiates at nucleotide position 495 and terminates at nucleotide position 1887 (FIG. 2) is completely deleted.

Construction of donor plasmids and recombinants expressing VP2 STC. A cassette containing the H6 promoted VP2 (STC) ORF was excised as a 1.5 kb SmaI-Asp718 fragment from pVP2-STC. The ends were repaired using Klenow polymerase and ligated into pF8 cut with SmaI to generate the pF8-STC donor plasmid.

Plasmid pF8-STC was used in in vitro recombination with TROVAC as the rescuing virus to generate recombinant vFP209. Expression analysis of the recombinants using a polyclonal IBDV serum from chicken indicated that the VP2 protein is expressed internally in CEF cells infected by the recombinant.

REFERENCES

1. Allan, W. H., J. T. Faragher, and G. A. Cullen, Vet. Rec. 90, 511–512 (1972).
2. Azad, A. A., S. A. Barrett, and K. J. Fahey, Virology 143, 35–44 (1985).
3. Azad, A. A., K. J. Fahey, S. Barrett, K. Erny and P. Hudson, Virology 149, 190–198 (1986).
4. Azad, A. A., M. N. Jagadish, M. A. Brown, and P. J. Hudson, Virology 161, 145–152 (1987).
5. Baxendale, W. and Lutticken, Dev. Biol. Stand. 51, 211–219 (1981).
6. Bayliss, C. D., U. Spies, K. Shaw, R. W. Peters, A. papageorgiou, H. Muller, and M. E. G. Boursnell, J. Gen. Virol. 71, 1303–1312 (1990).
7. Becht, H., H. Muller, and H. K. Muller, J. Gen. Virol. 69, 631–640 (1988).
8. Bertholet, C., R. Drillien, and R. Wittek, Proc. Natl. Acad. Sci. U. S. A. 82, 2096–2100 (1985).

9. Brown, F., Intervirology 25, 141–143 (1986).
10. Burkhardt, E. and H. Muller, Archives of Virology 94, 297–303 (1987).
11. Casadaban, M. J., A. Martinez-Arias, S. K. Shapira and J. Chou, Methods in Enzymol. 100, 293–307 (1983).
12. Clewell, D. B., J. Bacteriol. 110, 667–676 (1972).
13. Clewell, D. B. and D. R. Helinski, Proc. Natl. Acad. Sci. USA 62, 1159–1166 (1969).
14. Dobos, P., J. Virol. 32, 1046–1050 (1979).
15. Dobos, P., B. J. Hill, R. Hallett, D. T. Kells, H. Becht, and D. Teninges, J. Virol. 32, 593–605 (1979).
16. Duncan, R., E. Nagy, P. J. Krell and P. Dobos, J. Virol. 61, 3655–3664 (1987).
17. Edbauer, C., R. Weinberg, J. Taylor, A. Rey-Senelonge, J. F. Bouquet, P. Desmettre and E. Paoletti, Virology 179, 901–904 (1990).
18. Fahey, K. J., I. J. O'Donnell, and A. A. Azad, J. Gen. Virol. 66, 1479–1488 (1985a).
19. Fahey, K. J., I. J. O'Donnell, and T. J. Bagust, J. Gen. Virol. 66, 2693–2702 (1985b).
20. Fahey, K. J., K. Erny and J. Crooks, J. Gen. Virol. 70, 1473–1481 (1989).
21. Guo, P., S. Goebel, S. Davis, M. E. Perkus, B. Languet, P. Desmettre, G. Allen, and E. Paoletti, J. Virol. 63, 4189–4198 (1989).
22. Hudson, P. J., N. M. McKern, B. E. Power, and A. A. Azad, Nucl. Acids. Res. 14, 5001–5012 (1986).
23. Jackwood, D. J., Y. M. Saif, and J. H. Hughes, Avian Dis. 28, 990–1006 (1984).
24. Jagadish, M. N., V. J. Staton, P. J. Hudson, and A. A. Azad, J. Virol. 62, 1084–1087 (1988).
25. Kaufer, I. and E. Weiss, Infect. Immun. 27, 364–367 (1980).
26. Kibenge, F. S. B., A. S. Dhillon, and R. G. Russell, J. Gen. Virol. 69, 1757–1775 (1988).
27. Kibenge, F. S. B., D. J. Jackwood, and C. C. Mercado, J. Gen. Virol. 71, 569–577 (1990).
28. Langford, C. J., S. J. Edwards, G. L. Smith, G. F. Mitchell, B. Moss, D. J. Kemp, and R. F. Anders, Mol. Cell. Biol. 6, 3191–3199 (1986).
29. Ley, D. H., R. Yamamoto, and A. A. Bickford, Avian Diseases 23, 219–224 (1979).
30. Lucio, B. and S. B. Hitchner, Anian Dis. 23, 466–478 (1979).
31. Lukert, P. D. and S. B. Hitchner, In Diseases of Poultry 8th edition, eds. M. S. Hofstad, H. J. Barnes, B. W. Calnek, W. M. Reid and H. W. Yoder (Iowa State University press-Ames) pp. 566–576 (1984).
32. Lukert, P. D. and L. A. Mazariegos, J. Am. Vet. Med. Assoc. 187, 306 (ABSTR) (1985).
33. Lukert, P. D. and Y. M. Saif, In Diseases of Poultry 9th edition, eds. B. W. Calnek, H. J. Barnes, C. W. Beard, W. M. Reid and H. W. Yoder (Iowa State University press-Ames) pp. 648–663 (1991).
34. Macreadie, I. G., P. R. Vaughan, A. J. Chapman, N. M. McKern, M,B, Jagadish, H. G. Heine, C. W. Ward, K. J. Fahey, and A. A. Azad, Vaccine 8, 549–552 (1990).
35. Matthews, R. E. F., Intervirology 17, 42–44 (1982).
36. McFerran, J. B., M. S. McNulty, E. R. McKillop, T. J. Connor, R. M. McCracken, D. S. Collins, and G. M. Allen, Avian Pathol. 9, 395–404 (1980).
37. McNulty, M. S. and Y. M. Saif, Avian Dis. 32, 374–375 (1988).
38. Muller, H., Arch. Virol. 87, 191–203 (1986).
39. Muller, H. and H. Betch, J. Virol. 44, 384–392 (1982).
40. Nagy, E., R. Duncan, P. Krell, and P. Dobos, Virology 158, 211–217 (1987).
41. Panicali, D. and E. Paoletti, Proc. Natl. Acad. Sci. USA 79, 4927–4931 (1982).
42. Paoletti, E., B. R. Lipinskaks, C. Samsonoff, S. Mercer, and D. Panicali, Proc. Natl. Acad. Sci. U.S.A. 81, 193–197 (1984).
43. Perkus, M. E., K. Limbach, and E. Paoletti, J. Virol. 63, 3829–3836 (1989).
44. Piccini, A., M. E. Perkus, and E. Paoletti, In Methods in Enzymology, Vol. 153, eds. Wu, R., and Grossman, L., (Academic Press) pp. 545–563 (1987).
45. Sambrook, J., E. F. Fritsch, and T. Maniatis, In Molecular cloning: A laboratory manual, 2nd edition, (Cold Spring Harbor Press, New York) (1989).
46. Schat, K. A., B. Lucio, and J. C. Carlisle, Avian Dis. 25, 996–1004 (1981).
47. Shapira, S. K., J. Chou, F. V. Richaud, and M. J. Casadaban, Gene 25, 71–82 (1983).
48. Skeeles, J. K., P. D. Lukert, E. V. De Buysscher, O. J. Fletcher, and J. Brown, Avian Dis. 23, 95–106 (1979).
49. Snyder, D. B., D. P Lana, B. R. Cho, and W. W. Marquardt, Avian Dis. 32, 527–534 (1988).
50. Spies, U., H. Muller, and H. Becht, Virus Res. 8, 127–140 (1987).
51. Tartaglia, J., J. Winslow, S. Goebel, G. P. Johnson, J. Taylor, and E. Paoletti, J. Gen. Virol. 71, 1517–1524 (1990).
52. Taylor, J., R. Weinberg, Y. Kawaoka, R. Webster and E. Paoletti, Vaccine 6, 504–508 (1988).
53. Taylor, J., C. Edbauer, A. Rey-Senelonge, J. F. Bouquet, E. Norton, S. Goebel, P. Desmettre and E. Paoletti, J. Virol. 64, 1441–1450 (1990).
54. Vijaya, S., N. Elango, F. Zavala, and B. Moss, Mol. Cell. Biol. 8, 1709–1714 (1988).
55. Winterfield, R. W., A. M. Fadly, and A. Bickford. Avian Dis. 16, 622–632 (1972).
56. Winterfield, R. W., A. S. Dhillon, H. L. Thacker, L. J. Alby, Avian Dis. 24, 179–188 (1980).

---

What is claimed is:

1. A recombinant avipox virus comprising exogenous DNA from an infectious bursal disease virus inserted into a nonessential region of the avipox virus genome, wherein the exogenous DNA codes for and the recombinant avipox virus expresses infectious bursal disease virus structural protein VP2.

2. The recombinant avipox virus of claim 1 which is a fowlpox virus.

3. A poxvirus having virus-encoded genetic functions inactivated therein so that the virus has attenuated virulence; said poxvirus further comprising exogenous DNA from an infectious bursal disease virus which codes for and expresses an infectious bursal disease virus structural protein VP2, and is inserted by recombination in a nonessential region of the poxvirus genome; wherein said poxvirus is a fowlpox virus which has attenuated virulence through approximately 50 serial passages in chicken embryonated eggs followed by 25 passages on chicken embryo fibroblast cells, then subjecting the virus to four successive plaque purifications, and obtaining a plaque isolate and further amplifying the isolate in primary chick embryo fibroblast cells.

4. A vaccine comprising: a recombinant poxvirus of claim 3, or a recombinant avipox virus of any one of claims 1 or 2; and a suitable carrier; wherein the exogenous DNA encodes and the recombinant expresses cytoplasmically-directed VP2.

5. A method for inducing a protective immunological response in a host susceptible to infectious bursal disease virus comprising administering to the host a vaccine of claim 4.

6. The method of claim 5 wherein the host is a chicken.

7. A method for preparing an infectious bursal disease virus structural protein comprising introducing into cells of an in vitro cell culture a recombinant poxvirus of claim 3 or a recombinant avipox virus of any one of claims 1 or 2.

* * * * *

UNITED STATES PATENT AND TRADEMARK OFFICE
CERTIFICATE OF CORRECTION

PATENT NO. : 5,641,490
DATED : June 24, 1997
INVENTOR(S) : Paoletti et al.

It is certified that error appears in the above-indentified patent and that said Letters Patent is hereby corrected as shown below:

At Column 6, line 13: after "established." insert --TROVAC was deposited on February 6, 1997 under the terms of the Budapest Treaty with the American Type Culture Collection (ATCC), 12301 Parklawn Drive, Rockville, Maryland, 20852, USA, ATCC accession number VR-2553.--

Column 39, line 2
Claim 3: after "poxvirus is a" insert --TROVAC fowlpox virus or a--

Add Claim 8 as follows:

-- 8. The recombinant avipox virus of Claim 2 which is vFP115.--

Signed and Sealed this

Twenty-first Day of October 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 100 base pairs
        ( B ) TYPE: nucleic acid
        ( C ) STRANDEDNESS: single ( D ) TOPOLOGY: linear ( x i ) SEQUENCE DESCRIPTION: SEQ ID NO:1:

ACTTCATGGA GGTGGCCGAC CTCAACTCTC CCCTGAAGAT TGCAGGAGCA TTTGGCTTCA　　　60

AAGACATAAT CCGGGCTATA AGGAGGTGAG TCGACGGTAC　　　100

( 2 ) INFORMATION FOR SEQ ID NO:2:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CGTCGACTCA CCTCCTTATA GCCCGGATTA TGTCTTTGAA GCCAAATGCT CCTGCAATCT　　　60

TCAGGGGAGA GTTGAGGTCG GCCACCTCCA TGAAGT　　　96

( 2 ) INFORMATION FOR SEQ ID NO:3:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGATATCATG ACAAACCTGC AAGATCAAAC CCAACAGATT GTTCCGTTCA TACGGAGCCT　　　60

TCTGATGCCA ACAACCG　　　77

( 2 ) INFORMATION FOR SEQ ID NO:4:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GTCCGGTTGT TGGCATCAGA AGGCTCCGTA TGAACGGAAC AATCTGTTGG GTTTGATCTT　　　60

GCAGGTTTGT CATGATATCG　　　80

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GACCTTGAGT GAGTCGACGG TAC　　　23

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CGTCGACTCA CTCAAG　　　16

( 2 ) INFORMATION FOR SEQ ID NO:7:

( i ) SEQUENCE CHARACTERISTICS:
        ( A ) LENGTH: 3661 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
| GATATCTGTG | GTCTATATAT | ACTACACCCT | ACCGATATTA | ACCAACGAGT | TTCTCACAAG   60 |
| AAAACTTGTT | TAGTAGATAG | AGATTCTTTG | ATTGTGTTTA | AAAGAAGTAC | CAGTAAAAAG  120 |
| TGTGGCATAT | GCATAGAAGA | AATAAACAAA | AAACATATTT | CCGAACAGTA | TTTTGGAATT  180 |
| CTCCCAAGTT | GTAAACATAT | TTTTTGCCTA | TCATGTATAA | GACGTTGGGC | AGATACTACC  240 |
| AGAAATACAG | ATACTGAAAA | TACGTGTCCT | GAATGTAGAA | TAGTTTTTCC | TTTCATAATA  300 |
| CCCAGTAGGT | ATTGGATAGA | TAATAAATAT | GATAAAAAA | TATTATATAA | TAGATATAAG  360 |
| AAAATGATTT | TTACAAAAAT | AACCTATAAG | AACAATAAAA | ATATAATTAC | ATTTACGGAA  420 |
| AATAGCTGGT | TTTAGTTTAC | CAACTTAGAG | TAATTATCAT | ATTGAATCTA | TATTGTTTTT  480 |
| TAGTTATATA | AAAACATGAT | TAGCCCCCAA | TCGGATGAAA | ATATAAAGA | TGTTGAGAAT  540 |
| TTCGAATACA | ACAAAAGAG | GAATCGTACG | TTGTCCATAT | CCAAACATAT | AAATAAAAAT  600 |
| TCAAAGTAG | TATTATACTG | GATGTTAGA | GATCAACGTG | TACAAGATAA | TTGGGCTTTA  660 |
| ATTTACGCAC | AACGATTAGC | GTTAAAACTC | AAAATACCTC | TAAGAATATG | CTTTTGTGTC  720 |
| GTGCCAAAAT | TTCACACTAC | TACTTCTAGT | ACACTTTATG | TTTTAATAT | CCGGTCTTAA  780 |
| AGAAGTCGCG | GAAGAATGTA | AAAGACTATG | TATAGGGTTT | TCATTGATAT | ATGGCGTACC  840 |
| AAAAGTAATA | ATTCCGTGTA | TAGTAAAAAA | ATACAGAGTC | GGAGTAATCA | TAACGGATTT  900 |
| CTTTCCATTA | CGTGTTCCCG | AAAGATTAAT | GAAACAGACT | GTAATATCTC | TTCCAGATAA  960 |
| CATACCTTTT | ATACAAGTAG | ACGCTCATAA | TATAGTACCT | TGTTGGGAAG | CTTCTGATAA 1020 |
| AGAAGAATAC | GGTGCACGAA | CTTTAAGAAA | AAAGATATTT | GATAAATTAT | ATGAATATAT 1080 |
| GACAGAATTT | CCTGTTGTTC | GTAAACATCC | ATACGGTCCA | TTTTCTATAT | CTATTGCAAA 1140 |
| ACCCAAAAAT | ATATCATTAG | ACAAGACGGT | ATTACCCGTA | AAATGGGCAA | CGCCTGGAAC 1200 |
| AAAAGCTGGA | ATAATTGTTT | TAAAAGAATT | TATAAAAAAC | AGATTACCGT | CATACGACGC 1260 |
| GGATCATAAC | AATCCTACGT | GTGACGCTTT | GAGTAACTTA | TCTCCGTGGC | TACATTTTGG 1320 |
| TCATGTATCC | GCACAACGTG | TTGCCTTAGA | AGTATTAAAA | TGTATACGAG | AAAGCAAAAA 1380 |
| AAACGTTGAA | ACGTTTATAG | ATGAAATAAT | TGTAAGAAGA | GAACTATCGG | ATAATTTTTG 1440 |
| TTACTATAAC | AAACATTATG | ATAGTATCCA | GTCTACTCAT | TCATGGGTTA | GAAAAACATT 1500 |
| AGAAGATCAC | ATTAATGATC | CTAGAAAGTA | TATATATTCC | ATTAAACAAC | TCGAAAAAGC 1560 |
| GGAAACTCAT | GATCCTCTAT | GGAACGCGTC | ACAAATGCAG | ATGGTGAGAG | AAGGAAAAAT 1620 |
| GCATAGTTTT | TTACGAATGT | ATTGGGCTAA | GAAGATACTT | GAATGGACTA | GAACACCTGA 1680 |
| AGACGCTTTG | AGTTATAGTA | TCTATTTGAA | CAACAAGTAC | GAACTAGACG | GCACGGATCC 1740 |
| TAACGGATAC | GTAGGTTGTA | TGTGGTCTAT | TTGCGGATTA | CACGATAGAG | CGTGGAAAGC 1800 |
| AAGACCGATA | TTTGGAAAGA | TAAGATATAT | GAATTATGAG | AGTTCTAAGA | AGAAATTTGA 1860 |
| TGTTGCTGTA | TTTATACAGA | AATACAATTA | AGATAAATAA | TATACAGCAT | TGTAACCATC 1920 |
| GTCATCCGTT | ATACGGGGAA | TAATATTACC | ATACAGTATT | ATTAAATTTT | CTTACGAAGA 1980 |
| ATATAGATCG | GTATTTATCG | TTAGTTTATT | TTACATTTAT | TAATTAAACA | TGTCTACTAT 2040 |
| TACCTGTTAT | GGAAATGACA | AATTTAGTTA | TATAATTTAT | GATAAAATTA | AGATAATAAT 2100 |

```
AATGAAATCA  AATAATTATG  TAAATGCTAC  TAGATTATGT  GAATTACGAG  GAAGAAAGTT       2160

TACGAACTGG  AAAAAATTAA  GTGAATCTAA  AATATTAGTC  GATAATGTAA  AAAAAATAAA       2220

TGATAAAACT  AACCAGTTAA  AAACGGATAT  GATTATATAC  GTTAAGGATA  TTGATCATAA       2280

AGGAAGAGAT  ACTTGCGGTT  ACTATGTACA  CCAAGATCTG  GTATCTTCTA  TATCAAATTG       2340

GATATCTCCG  TTATTCGCCG  TTAAGGTAAA  TAAAATTATT  AACTATTATA  TATGTAATGA       2400

ATATGATATA  CGACTTAGCG  AAATGGAATC  TGATATGACA  GAAGTAATAG  ATGTAGTTGA       2460

TAAATTAGTA  GGAGGATACA  ATGATGAAAT  AGCAGAAATA  ATATATTTGT  TTAATAAATT       2520

TATAGAAAAA  TATATTGCTA  ACATATCGTT  ATCAACTGAA  TTATCTAGTA  TATTAAATAA       2580

TTTTATAAAT  TTTATAAATT  TTAATAAAAA  ATACAATAAC  GACATAAAGA  TATTTAATCT       2640

TTAATTCTTG  ATCTGAAAAA  CACATCTATA  AAACTAGATA  AAAGTTATT   CGATAAAGAT       2700

AATAATGAAT  CGAACGATGA  AAAATTGGAA  ACAGAAGTTG  ATAAGCTAAT  TTTTTTCATC       2760

TAAATAGTAT  TATTTTATTG  AAGTACGAAG  TTTTACGTTA  GATAAATAAT  AAAGGTCGAT       2820

TTTTACTTTG  TTAAATATCA  AATATGTCAT  TATCTGATAA  AGATACAAAA  ACACACGGTG       2880

ATTATCAACC  ATCTAACGAA  CAGATATTAC  AAAAAATACG  TCGGACTATG  GAAAACGAAG       2940

CTGATAGCCT  CAATAGAAGA  AGCATTAAAG  AAATTGTTGT  AGATGTTATG  AAGAATTGGG       3000

ATCATCCTCA  ACGAAGAAAT  AGATAAAGTT  CTAAACTGGA  AAAATGATAC  ATTAAACGAT       3060

TTAGATCATC  TAAATACAGA  TGATAATATT  AAGGAAATCA  TACAATGTCT  GATTAGAGAA       3120

TTTGCGTTTA  AAAAGATCAA  TTCTATTATG  TATAGTTATG  CTATGGTAAA  ACTCAATTCA       3180

GATAACGAAC  ATTGAAAGAT  AAAATTAAGG  ATTATTTTAT  AGAAACTATT  CTTAAAGACA       3240

AACGTGGTTA  TAAACAAAAG  CCATTACCCG  GATTGGAAAC  TAAAATACTA  GATAGTATTA       3300

TAAGATTTTA  AAAACATAAA  ATTAATAGGT  TTTTATAGAT  TGACTTATTA  TATACAATAT       3360

GGATAAAAGA  TATATATCAA  CTAGAAAGTT  GAATGACGGA  TTCTTAATTT  TATATTATGA       3420

TTCAATAGAA  ATTATTGTCA  TGTCGTGTAA  TCATTTTATA  AATATATCAG  CGTTACTAGC       3480

TAAGAAAAAC  AAGGACTTTA  ATGAATGGCT  AAAGATAGAA  TCATTTAGAG  AAATAATAGA       3540

TACTTTAGAT  AAAATTAATT  ACGATCTAGG  ACAACGATAT  TGTGAAGAAC  TTACGGCGCA       3600

TCACATTCCA  GTGTAATTAT  TGAGGTCAAA  GCTAGTAACT  TAATAGATGA  CAGGACAGCT       3660

G                                                                            3661
```

( 2 ) INFORMATION FOR SEQ ID NO:8:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CTAGACACTT  TATGTTTTTT  AATATCCGGT  CTTAAAAGCT  TCCCGGGGGA  TCCTTATACG        60

GGGAATAAT                                                                    69
```

( 2 ) INFORMATION FOR SEQ ID NO:9:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

-continued

| ATTATTCCCC | GTATAAGGAT | CCCCCGGGAA | GCTTTTAAGA | CCGGATATTA | AAAAACATAA | 60 |
| AGTGT | | | | | | 65 |

( 2 ) INFORMATION FOR SEQ ID NO:10:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

| GATCAGAAAA | ACTAGCTAGC | TAGTACGTAG | TTAACGTCGA | CCTGCAGAAG | CTTCTAGCTA | 60 |
| GCTAGTTTTT | AT | | | | | 72 |

( 2 ) INFORMATION FOR SEQ ID NO:11:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

| AGCTATAAAA | ACTAGCTAGC | TAGAAGCTTC | TGCAGGTCGA | CGTTAACTAC | GTACTAGCTA | 60 |
| GCTAGTTTTT | CT | | | | | 72 |

( 2 ) INFORMATION FOR SEQ ID NO:12:

( i ) SEQUENCE CHARACTERISTICS:
        ( A ) LENGTH: 3659 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

| GATATCTGTG | GTCTATATAT | ACTACACCCT | ACCGATATTA | ACCAACGAGT | TTCTCACAAG | 60 |
| AAAACTTGTT | TAGTAGATAG | AGATTCTTTG | ATTGTGTTTA | AAGAAGTAC | CAGTAAAAAG | 120 |
| TGTGGCATAT | GCATAGAAGA | AATAAACAAA | AACATATTT | CCGAACAGTA | TTTTGGAATT | 180 |
| CTCCCAAGTT | GTAAACATAT | TTTTGCCTA | TCATGTATAA | GACGTTGGGC | AGATACTACC | 240 |
| AGAAATACAG | ATACTGAAAA | TACGTGTCCT | GAATGTAGAA | TAGTTTTTCC | TTTCATAATA | 300 |
| CCCAGTAGGT | ATTGGATAGA | TAATAAATAT | GATAAAAAA | TATTATATAA | TAGATATAAG | 360 |
| AAAATGATTT | TTACAAAAAT | ACCTATAAGA | ACAATAAAAA | TATAATTACA | TTTACGGAAA | 420 |
| ATAGCTGGTT | TTAGTTTACC | AACTTAGAGT | AATTATCATA | TTGAATCTAT | ATTGTTTTTT | 480 |
| AGTTATATAA | AAACATGATT | AGCCCCCAAT | CGGATGAAAA | TATAAAAGAT | GTTGAGAATT | 540 |
| TCGAATACAA | CAAAAGAGG | AATCGTACGT | TGTCCATATC | CAAACATATA | AATAAAAATT | 600 |
| CAAAAGTAGT | ATTATACTGG | ATGTTAGAG | ATCAACGTGT | ACAAGATAAT | TGGGCTTTAA | 660 |
| TTTACGCACA | ACGATTAGCG | TTAAAACTCA | AAATACCTCT | AAGAATATGC | TTTTGTGTCG | 720 |
| TGCCAAAATT | TCACACTACT | ACTTCTAGAC | ACTTTATGTT | TTAATATCC | GGTCTTAAAG | 780 |
| AAGTCGCGGA | AGAATGTAAA | AGACTATGTA | TAGGGTTTTC | ATTGATATAT | GGCGTACCAA | 840 |
| AAGTAATAAT | TCCGTGTATA | GTAAAAAAAT | ACAGAGTCGG | AGTAATCATA | ACGGATTTCT | 900 |
| TTCCATTACG | TGTTCCCGAA | AGATTAATGA | AACAGACTGT | AATATCTCTT | CCAGATAACA | 960 |
| TACCTTTTAT | ACAAGTAGAC | GCTCATAATA | TAGTACCTTG | TTGGGAAGCT | TCTGATAAAG | 1020 |
| AAGAATACGG | TGCACGAACT | TTAAGAAAAA | AGATATTTGA | TAAATTATAT | GAATATATGA | 1080 |

```
CAGAATTTCC TGTTGTTCGT AAACATCCAT ACGGTCCATT TTCTATATCT ATTGCAAAAC    1140
CCAAAAATAT ATCATTAGAC AAGACGGTAT TACCCGTAAA ATGGGCAACG CCTGGAACAA    1200
AAGCTGGAAT AATTGTTTTA AAAGAATTTA TAAAAAACAG ATTACCGTCA TACGACGCGG    1260
ATCATAACAA TCCTACGTGT GACGCTTTGA GTAACTTATC TCCGTGGCTA CATTTTGGTC    1320
ATGTATCCGC ACAACGTGTT GCCTTAGAAG TATTAAAATG TATACGAGAA AGCAAAAAAA    1380
ACGTTGAAAC GTTTATAGAT GAAATAATTG TAAGAAGAGA ACTATCGGAT AATTTTGTT    1440
ACTATAACAA ACATTATGAT AGTATCCAGT CTACTCATTC ATGGGTTAGA AAAACATTAG    1500
AAGATCACAT TAATGATCCT AGAAAGTATA TATATTCCAT TAAACAACTC GAAAAGCGG    1560
AAACTCATGA TCCTCTATGG AACGCGTCAC AAATGCAGAT GGTGAGAGAA GGAAAAATGC    1620
ATAGTTTTTT ACGAATGTAT TGGGCTAAGA AGATACTTGA ATGGACTAGA ACACCTGAAG    1680
ACGCTTTGAG TTATAGTATC TATTTGAACA ACAAGTACGA ACTAGACGGC ACGGATCCTA    1740
ACGGATACGT AGGTTGTATG TGGTCTATTT GCGGATTACA CGATAGAGCG TGGAAAGCAA    1800
GACCGATATT TGGAAAGATA AGATATATGA ATTATGAGAG TTCTAAGAAG AAATTTGATG    1860
TTGCTGTATT TATACAGAAA TACAATTAAG ATAAATAATA TACAGCATTG TAACCATCGT    1920
CATCCGTTAT ACGGGGAATA ATATTACCAT ACAGTATTAT TAAATTTCT TACGAAGAAT    1980
ATAGATCGGT ATTTATCGTT AGTTTATTTT ACATTTATTA ATTAAACATG TCTACTATTA    2040
CCTGTTATGG AAATGACAAA TTTAGTTATA TAATTTATGA TAAAATTAAG ATAATAATAA    2100
TGAAATCAAA TAATTATGTA AATGCTACTA GATTATGTGA ATTACGAGGA AGAAAGTTTA    2160
CGAACTGGAA AAAATTAAGT GAATCTAAAA TATTAGTCGA TAATGTAAAA AAAATAAATG    2220
ATAAAACTAA CCAGTTAAAA ACGGATATGA TTATATACGT TAAGGATATT GATCATAAAG    2280
GAAGAGATAC TTGCGGTTAC TATGTACACC AAGATCTGGT ATCTTCTATA TCAAATTGGA    2340
TATCTCCGTT ATTCGCCGTT AAGGTAAATA AAATTATTAA CTATTATATA TGTAATGAAT    2400
ATGATATACG ACTTAGCGAA ATGGAATCTG ATATGACAGA AGTAATAGAT GTAGTTGATA    2460
AATTAGTAGG AGGATACAAT GATGAAATAG CAGAAATAAT ATATTTGTTT AATAAATTTA    2520
TAGAAAAATA TATTGCTAAC ATATCGTTAT CAACTGAATT ATCTAGTATA TTAAATAATT    2580
TTATAAATTT TATAAATTTT AATAAAAAAT ACAATAACGA CATAAAGATA TTTAATCTTT    2640
AATTCTTGAT CTGAAAAACA CATCTATAAA ACTAGATAAA AAGTTATTCG ATAAAGATAA    2700
TAATGAATCG AACGATGAAA AATTGGAAAC AGAAGTTGAT AAGCTAATTT TTTTCATCTA    2760
AATAGTATTA TTTTATTGAA GTACGAAGTT TTACGTTAGA TAAATAATAA AGGTCGATTT    2820
TTACTTTGTT AAATATCAAA TATGTCATTA TCTGATAAAG ATACAAAAAC ACACGGTGAT    2880
TATCAACCAT CTAACGAACA GATATTACAA AAAATACGTC GGACTATGGA AAACGAAGCT    2940
GATAGCCTCA ATAGAAGAAG CATTAAAGAA ATTGTTGTAG ATGTTATGAA GAATTGGGAT    3000
CATCCTCAAC GAAGAAATAG ATAAAGTTCT AAACTGGAAA AATGATACAT TAAACGATTT    3060
AGATCATCTA AATACAGATG ATAATATTAA GGAAATCATA CAATGTCTGA TTAGAGAATT    3120
TGCGTTTAAA AAGATCAATT CTATTATGTA TAGTTATGCT ATGGTAAAAC TCAATTCAGA    3180
TAACGAACAT TGAAAGATAA AATTAAGGAT TATTTTATAG AAACTATTCT TAAAGACAAA    3240
CGTGGTTATA AACAAAGCC ATTACCCGGA TTGGAAACTA AATACTAGA TAGTATTATA    3300
AGATTTTAAA AACATAAAAT TAATAGGTTT TTATAGATTG ACTTATTATA TACAATATGG    3360
ATAAAGATA TATATCAACT AGAAGTTGA ATGACGGATT CTTAATTTTA TATTATGATT    3420
CAATAGAAAT TATTGTCATG TCGTGTAATC ATTTTATAAA TATATCAGCG TTACTAGCTA    3480
```

| AGAAAAACAA | GGACTTTAAT | GAATGGCTAA | AGATAGAATC | ATTTAGAGAA | ATAATAGATA | 3540 |
| CTTTAGATAA | AATTAATTAC | GATCTAGGAC | AACGATATTG | TGAAGAACTT | ACGGCGCATC | 3600 |
| ACATTCCAGT | GTAATTATTG | AGGTCAAAGC | TAGTAACTTA | ATAGATGACA | GGACAGCTG | 3659 |

( 2 ) INFORMATION FOR SEQ ID NO:13:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

| AATTAACCCG | GGATCCAAGC | TTCTAGCTAG | CTAATTTTA | TAGCGGCCGC | TATAATCGTT | 60 |
| AACTTATTAG | | | | | | 70 |

( 2 ) INFORMATION FOR SEQ ID NO:14:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

| CTAGCTAGAA | GCTTGGATCC | CGGGTTAATT | AATTAATAAA | AAGCGGCCGC | GTTAAAGTAG | 60 |
| AAAAATG | | | | | | 67 |

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GTTACATATG TACAGAATCT GATCATAG             28

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GCTAGAATTC TCTTAGTTTT TATAGTTG             28

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AAGGTAGTAC TGGCGTCC             18

( 2 ) INFORMATION FOR SEQ ID NO:18:

( i ) SEQUENCE CHARACTERISTICS:

( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:18:

TTATCGCGAT ATCCGTTAAG TTTGTATCGT AATATGTTCC CTCACAATCC ACGA    54

( 2 ) INFORMATION FOR SEQ ID NO:19:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:19:

TAAAAGCTTT TAATTAATTA GTCATC    26

( 2 ) INFORMATION FOR SEQ ID NO:20:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:20:

TAACCCGGGC GATACAAACT TAACGG    26

( 2 ) INFORMATION FOR SEQ ID NO:21:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( x i ) SEQUENCE DESCRIPTION: SEQ ID NO:21:

GATCCCGGTA CCTCTAATGC TGATCATCCG AACCGCGCTG ACACTGAGCT GTACAAACCT    60

GCAAGATCAA AC    72

( 2 ) INFORMATION FOR SEQ ID NO:22:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:22:

GGACGCCGGT CCGGTTGTTG GCATC    25

( 2 ) INFORMATION FOR SEQ ID NO:23:

( i ) SEQUENCE CHARACTERISTICS:
( A ) LENGTH: 112 base pairs
( B ) TYPE: nucleic acid
( C ) STRANDEDNESS: single
( D ) TOPOLOGY: linear ( x i ) SEQUENCE DESCRIPTION: SEQ ID NO:23:

GTGAGTACTT CATGGAGGTG GCCGACCTCA ACTCTCCCCT GAAGATTGCA GGAGCATTTG    60

GCTTCAAAGA CATAATCCGG GCTATAAGGA GGATCGTTTT AACTGTCATA TC    112

( 2 ) INFORMATION FOR SEQ ID NO:24:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:24:

TTAGGATCCT CATATTTTTG TAGTGGCTCT C  31

( 2 ) INFORMATION FOR SEQ ID NO:25:

( i ) SEQUENCE CHARACTERISTICS:
 ( A ) LENGTH: 42 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:25:

TACACACTGC AGAGCAATGG GAACCTCAAG TTCGATCAGA TG  42

( 2 ) INFORMATION FOR SEQ ID NO:26:

( i ) SEQUENCE CHARACTERISTICS:
 ( A ) LENGTH: 39 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:26:

GAAACACGAG CTCTCCCCCA ACGCTGAGGC TTGTGATAG  39

( 2 ) INFORMATION FOR SEQ ID NO:27:

( i ) SEQUENCE CHARACTERISTICS:
 ( A ) LENGTH: 155 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:27:

GGAAGAGCTC GTGTTTCAAA CAAGCGTCCA AGGCCTTGTA CTGGGCGCCA CCATCTACTT  60
TATAGGCTTT GATGGGACTA CGGTAATCAC CAGAGCTGTA GCCGCAGATA ATGGGCTGAC  120
GGCCGGCACC GACAATCTTA TGCCATTCAA TCTTG  155

( 2 ) INFORMATION FOR SEQ ID NO:28:

( i ) SEQUENCE CHARACTERISTICS:
 ( A ) LENGTH: 155 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:28:

CCACCATGGA TCGTCACTGC TAGGCTCCCA CTTGCCGACC ATGACATCTG ATCCCTGCC  60
TGACCACCAC TTTTGGAGGT CACTACCTCC AGTTTGATGG ATGTGATTGG CTGGGTTATC  120
TCATTGGTTG GAATGACAAG ATTGAATGGC ATAAG  155

( 2 ) INFORMATION FOR SEQ ID NO:29:

( i ) SEQUENCE CHARACTERISTICS:
 ( A ) LENGTH: 26 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:29:

GGGAGAGCTC GTGTTTCAAA CAAGCG 26

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CCACCATGGA TCGTCACTGC 20

( 2 ) INFORMATION FOR SEQ ID NO:31:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

AACATATTTC CGAACAG 17

( 2 ) INFORMATION FOR SEQ ID NO:32:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

TCCAAGCTTT CGCGACCCGG GTTTTATTA GCTAATTAGC AATATAGATT CAATATG 57

( 2 ) INFORMATION FOR SEQ ID NO:33:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

ATCAAGCTTG GATCCCTCGA GTTTTATTG ACTAGTTAAT CATAAGATAA ATAATATACA 60

GC 62

( 2 ) INFORMATION FOR SEQ ID NO:34:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GATATAGAAG ATACCAG 17